US011581075B2

(12) United States Patent
Matthews et al.

(10) Patent No.: US 11,581,075 B2
(45) Date of Patent: *Feb. 14, 2023

(54) SYSTEMS AND METHODS FOR DETECTING DOCUMENTATION DROP-OFFS IN CLINICAL DOCUMENTATION

(71) Applicant: Iodine Software, LLC, Austin, TX (US)

(72) Inventors: Jonathan Matthews, Dripping Springs, TX (US); W. Lance Eason, Austin, TX (US); William Chan, Austin, TX (US); Michael Kadyan, Austin, TX (US); Frances Elizabeth Jurcak, Plymouth, MI (US); Timothy Paul Harper, Austin, TX (US)

(73) Assignee: Iodine Software, LLC, Austin, TX (US)

( * ) Notice: Subject to any disclaimer, the term of this patent is extended or adjusted under 35 U.S.C. 154(b) by 234 days.

This patent is subject to a terminal disclaimer.

(21) Appl. No.: 17/129,598

(22) Filed: Dec. 21, 2020

(65) Prior Publication Data
US 2021/0151144 A1      May 20, 2021

Related U.S. Application Data

(63) Continuation of application No. 16/185,784, filed on Nov. 9, 2018, now Pat. No. 10,886,013.
(Continued)

(51) Int. Cl.
*G16H 10/60* (2018.01)
*G06N 20/00* (2019.01)
(Continued)

(52) U.S. Cl.
CPC .......... *G16H 10/60* (2018.01); *G06F 40/205* (2020.01); *G06F 40/242* (2020.01); *G06F 40/30* (2020.01);
(Continued)

(58) Field of Classification Search
CPC ..... G16H 10/60; G06F 40/205; G06F 40/242; G06F 40/30; G06F 3/0483; G06F 3/0482; G06N 20/00
See application file for complete search history.

(56) References Cited

U.S. PATENT DOCUMENTS

| 10,886,013 B1 | 1/2021 | Matthews | |
|---|---|---|---|
| 2013/0297348 A1 * | 11/2013 | Cardoza | G16H 40/20 705/3 |

FOREIGN PATENT DOCUMENTS

| WO | WO-2017079012 A1 * | 5/2017 | ............. G06Q 50/22 |

OTHER PUBLICATIONS

Garla, Vijay. Kernel methods and semantic techniques for clinical text classification. ProQuest Dissertations and Theses ProQuest Dissertations Publishing. (2012) (Year: 2012).*

(Continued)

*Primary Examiner* — Linh Giang Le
(74) *Attorney, Agent, or Firm* — Sprinkle IP Law Group

(57) ABSTRACT

In clinical documentation, mere documentation of a condition in a patient's records may not be enough. To be considered sufficiently documented, the patient's record needs to show that no documentation drop-offs (DDOs) have occurred over the course of the patient's stay. However, DDOs can be extremely difficult to detect. To solve this problem, the invention trains time-sensitive deep learning (DL) models on a per condition basis using actual and/or synthetic patient data. Utilizing an ontology, grouped concepts can be generated on the fly from real-time hospital data and used to generate time-series data that can then be analyzed by trained time-sensitive DL models to determine whether a DDO for a condition has occurred during the stay. Non-time-sensitive models can be used to detect all the conditions documented during the stay. Outcomes from the (Continued)

models can be compared to determine whether to notify a user that a DDO has occurred.

20 Claims, 10 Drawing Sheets

Related U.S. Application Data

(60) Provisional application No. 62/586,629, filed on Nov. 15, 2017.

(51) Int. Cl.
*G06F 40/30* (2020.01)
*G06F 40/205* (2020.01)
*G06F 40/242* (2020.01)
G06F 3/0482 (2013.01)
G06F 3/0483 (2013.01)

(52) U.S. Cl.
CPC ............ *G06N 20/00* (2019.01); *G06F 3/0482* (2013.01); *G06F 3/0483* (2013.01)

(56) References Cited

OTHER PUBLICATIONS

Notice of Allowance for U.S. Appl. No. 16/185,784, dated Sep. 2, 2020, 7 pgs.

* cited by examiner

| Johnny Special — 801 | Patient Info ▼ | DRG: 853 ▼ | | | Query | Complete | More | Worksheet |
|---|---|---|---|---|---|---|---|---|
| MRN: | | Complaint: ACUTE CHOLE... | Current Owner | | | Payer: MEDICARE PART B... | | |

Spotlight

Male | 77 years | Encounter:

▼ Possible Conditions: 5

Important: *The condition(s) displayed below may or may not exist. Please use your professional judgement when reviewing.* Read More

| | |
|---|---|
| Acute blood loss anemia | Evidence ▭▭ Documentation ▭▭ |
| Hypernatremia | Evidence ▭▭ Documentation ▭▭ |
| Renal failure | Evidence ▭▭ Documentation ▭▭ |
| Respiratory failure | Evidence ▭▭ Documentation ▭▭ |
| Sepsis | Evidence ▭▭ Documentation ▭▭ |

▼ Special Events: 6

- Discharge Ordered
- Venous Doppler
- Lung Scan
- Blood product
- Low HCT/HGB
- [GMLOS] High LOS ← 830

▼ Documentation Warnings: 1

⚠ Sepsis - Documentation Drop-off

810 — [sidebar: Timeline, Opportunities 820, Documents, Labs and Vitals, Grouper, Queries]

SYSTEMS AND METHODS FOR DETECTING DOCUMENTATION DROP-OFFS IN CLINICAL DOCUMENTATION

CROSS-REFERENCE TO RELATED APPLICATION(S)

This application is a continuation of, and claims a benefit of priority under 35 U.S.C. § 120 of, U.S. patent application Ser. No. 16/185,784, filed Nov. 9, 2018, entitled "SYSTEMS AND METHODS FOR DETECTING DOCUMENTATION DROP-OFFS IN CLINICAL DOCUMENTATION," issued as U.S. Pat. No. 10,886,013, which claims a benefit of priority under 35 U.S.C. § 119(e) from U.S. Provisional Application No. 62/586,629, filed Nov. 15, 2017, entitled "SYSTEMS AND METHODS FOR DETECTING DOCUMENTATION DROP-OFFS IN CLINICAL DOCUMENTATION," which are fully incorporated by reference herein for all purposes.

TECHNICAL FIELD

This disclosure relates generally to clinical documentation improvement (CDI) technology. More particularly, embodiments disclosed herein relate to systems, methods, and computer program products for enhanced CDI data mining and processing using a combination of time-sensitive and non-time-sensitive models, useful for detecting documentation drop-offs in clinical documentation.

BACKGROUND OF THE RELATED ART

Clinical documentation improvement (CDI) refers to a process used in healthcare facilities such as hospitals. CDI can facilitate the accurate representation of a patient's clinical status that translates into coded data, which can then be translated into hospital quality report cards, physician report cards, reimbursement, public health data, and so on. A health information management (HIM) or CDI specialist's job is to review the information that a physician has documented (clinical documentation) about a patient in order to ensure that the documentation is accurate and complete. This process can be labor intensive because it requires the CDI specialist to understand the clinical needs of the patient and is able to find the gaps in the documentation in the patient's chart.

Traditionally, a static data processing model is used by a computerized CDI system to determine whether a condition of a patient is mentioned in the patient's clinical documentation (e.g., a physician's report), but not coded (e.g., using the Diagnosis-Related Group (DRG) code system) for the purposes of payment. If so, a CDI specialist is prompted to review for a chance to improve the clinical documentation. However, this static approach is insufficient to meet payer requirements (e.g., government regulation on Medicare) for clinical documentation.

SUMMARY OF THE DISCLOSURE

Embodiments disclosed herein can address the aforementioned drawbacks and provide additional technical solutions and benefits. As discussed above, a CDI specialist's job is to review the information that a physician has documented (clinical documentation) about a patient in order to ensure that the documentation is accurate and complete. A CDI system may facilitate this process by processing real-time medical data provided by a hospital (e.g., pushed from a hospital system over a network) to identify any condition of a patient that is documented in a physician's report but the documentation is not sufficient for coding purposes based on the patient's records and/or any condition that likely exists based on information contained in the patient's records, but that is not specifically documented in the patient's records. The CDI system may notify a CDI specialist (e.g., via email, text message, notification, personal portal, etc.) so that the CDI specialist can review the clinical documentation associated with the patient and, if appropriate, ask a healthcare provider or physician to describe a condition and/or a DRG code for the condition to the patient's records to improve the clinical documentation of the patient's records.

However, as discussed above, sometimes the mere documentation of a condition in the patient's records is not enough. For a condition to be considered well-documented, the patient's record would need to show that the condition is documented over the course of the patient's stay. While the CDI system can detect the existence of a patient's condition utilizing a static prediction model, the existence, in and by itself, does not necessary mean that the condition had been sufficiently documented, from time to time, over the course of the patient's entire stay. This is referred to as a CDI DDO.

CDI DDOs are a unique problem in the field of CDI technology and an obstacle in meeting the government regulation (e.g., Medicaid) for clinical documentation. In order for a patient's condition to meet the medical claim coding (e.g., DRG) guidelines, the clinical documentation must show that the condition is sufficiently documented at various time points over the course of the patient's stay (e.g., entry of the condition, treatment of the condition, resolution of the condition, follow-up on the condition, and so on, all the way to the discharge of the patient). Otherwise, even if a claim is submitted for payment, it may be denied. However, DDOs are difficult to spot from mountains of real-time patient data continuously streamed from the hospital. Essentially, detection of DDOs is akin to looking for something that is missing in the incoming patient data, which is significantly more difficult than looking for something like a patient condition that either already exists in the patient data or can be mined from the patient data.

An object of the invention disclosed herein is to reduce, if not eliminate, CDI DDOs by processing clinical documentation using a time-sensitive machine learning (ML) model to detect a patient's condition that exists, but that is not sufficiently documented in the patient's records during the patient's stay in the hospital. A static, non-time-sensitive prediction model such as the gradient boosting model (GBM) can be utilized to validate the existence of the condition and/or make the time-sensitive ML model runs more efficiently. These and other objects can be realized in a new system, method, and computer program product for detecting CDI DDOs.

Particularly, the invention is directed to solving a unique DDO problem in the field of CDI technology. A time-based deep learning (DL) model is trained on a per condition basis using actual and/or synthetic patient data as the training data. The training data may contain a huge amount of historical patient records which had been specifically identified as having a particular condition or not having the particular condition. In this way, a machine running the time-based DL model can be trained to learn to identify patient conditions that may exist in the incoming patient data. As skilled artisans can appreciate, a different set of patient data may be used as the test data to test the accuracy of the time-based DL model in its ability to correctly identify a patient condition from the test data. The results can then be used to fine tune and improve the time-based DL model. The time-based DL model thus trained can then be used to identify any condition that a patient likely has within a period of time and output a list of condition(s) for that patient. A static prediction model is trained on the same training and test data, also on a per condition basis. The trained static prediction model can be used to determine and maintain a list of conditions associated with the patient during the patient's stay. Outputs from both types of models are compared to identify/detect any patient-specific condition that may be documented at some point in time in the clinical documentation, but not sufficiently documented over the course of the patient's stay (a DDO).

An alert or notification on the DDO may be generated and communicated to a CDI specialist through a user interface. The CDI specialist can inform or request the patient's attending physician or health care provider to update the patient's electronic medical records (EMR) at the hospital to remedy the DDO. The updated EMR for the patient is entered into the hospital's system which sends it to the CDI system (e.g., through the next push of real-time medical data to the CDI system). Responsive to receiving the updated documentation, the CDI system, in turn, can parse out the updated EMR for the patient from the incoming real-time medical data and use the updated information associated with the patient to recalculate the prediction on the DDO for the patient's records, thereby completing the loop of clinical documentation improvement. The patient's condition is now considered to be sufficiently documented and the DDO problem is prevented or eliminated.

One embodiment comprises a system comprising a processor and a non-transitory computer-readable storage medium that stores computer instructions translatable by the processor to perform a method substantially as described herein. Another embodiment comprises a computer program product having a non-transitory computer-readable storage medium that stores computer instructions translatable by a processor to perform a method substantially as described herein. Numerous other embodiments are also possible.

These, and other, aspects of the disclosure will be better appreciated and understood when considered in conjunction with the following description and the accompanying drawings. It should be understood, however, that the following description, while indicating various embodiments of the disclosure and numerous specific details thereof, is given by way of illustration and not of limitation. Many substitutions, modifications, additions, and/or rearrangements may be made within the scope of the disclosure without departing from the spirit thereof, and the disclosure includes all such substitutions, modifications, additions, and/or rearrangements.

BRIEF DESCRIPTION OF THE DRAWINGS

The drawings accompanying and forming part of this specification are included to depict certain aspects of the invention. A clearer impression of the invention, and of the components and operation of systems provided with the invention, will become more readily apparent by referring to the exemplary, and therefore non-limiting, embodiments illustrated in the drawings, wherein identical reference numerals designate the same components. Note that the features illustrated in the drawings are not necessarily drawn to scale.

FIGS. 8A-8E are diagrammatic representation of screenshots of a user interface of a real-time medical communication system according to some embodiments.

DETAILED DESCRIPTION

The invention and the various features and advantageous details thereof are explained more fully with reference to the non-limiting embodiments that are illustrated in the accompanying drawings and detailed in the following description. Descriptions of well-known starting materials, processing techniques, components and equipment are omitted so as not to unnecessarily obscure the invention in detail. It should be understood, however, that the detailed description and the specific examples, while indicating some embodiments of the invention, are given by way of illustration only and not by way of limitation. Various substitutions, modifications, additions, and/or rearrangements within the spirit and/or scope of the underlying inventive concept will become apparent to those skilled in the art from this disclosure.

Figure 1:
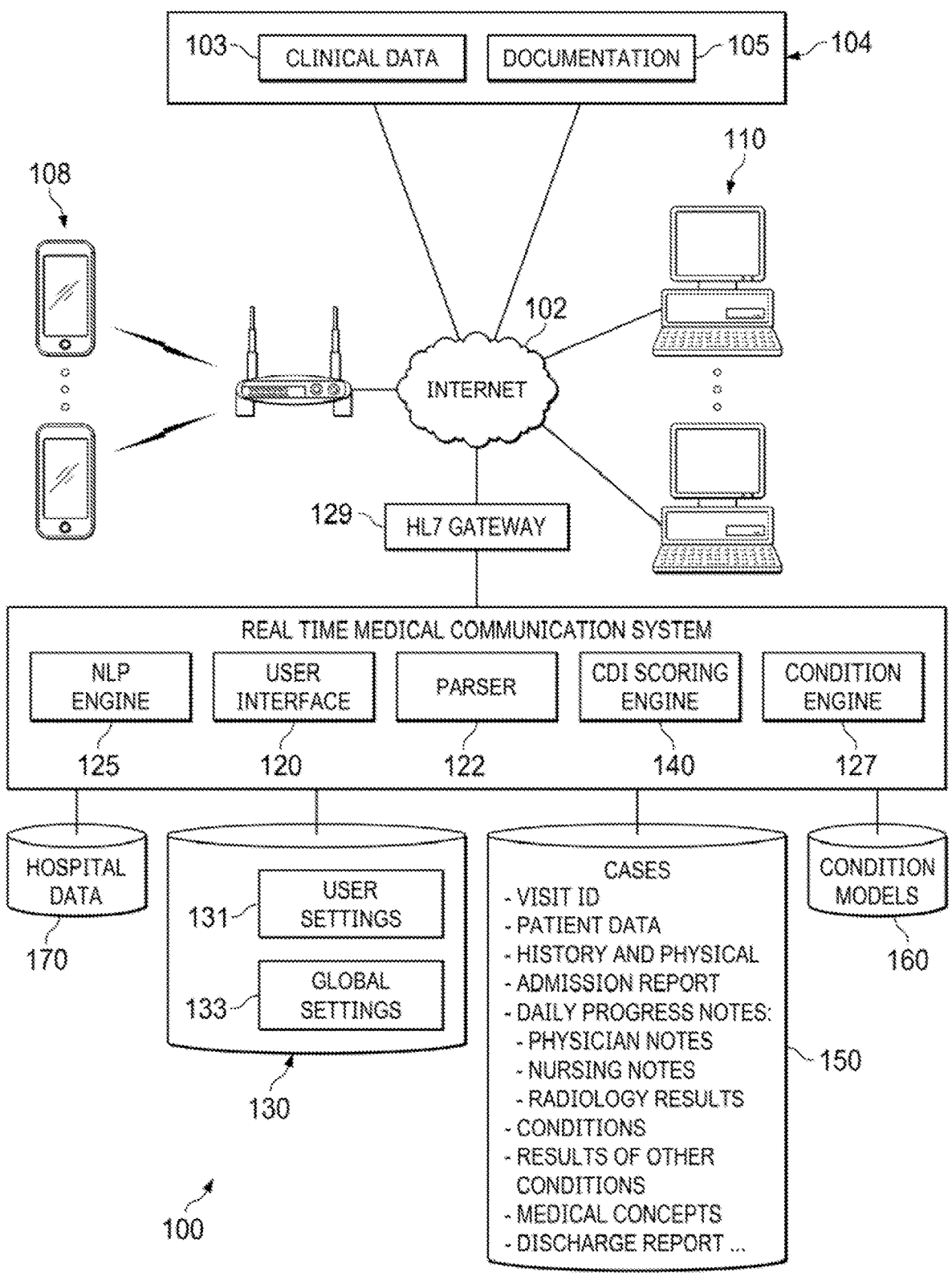
FIG. 1 depicts a diagrammatic representation of an example of a real-time network-based medical communication system architecture for implementing embodiments disclosed herein.

FIG. 1 is a diagrammatic representation of one example of a real-time network-based medical communication system architecture according to some embodiments. In the example illustrated, real-time medical communication system 100 is communicatively connected to hospital data source(s) 104 and various computing devices 108 . . . 110 over network 102 such as the Internet, a public network, or a wide area network.

System 100 may be embodied on a single or multiple server machine(s) and may include a plurality of system components, for instance, user interface 120, parser 122, condition engine 127, Natural Language Processing (NLP) engine 125, CDI scoring engine 140, and data store(s) storing hospital data 170, settings 130, patient cases 150, condition models 160, etc. There data stores can implement any suitable database management systems, such as relational database management systems (RDBMS), and programming languages, such as Structured Query Language (SQL) suitable for storing, accessing, and managing data communicated to and from, as well as generated and/or used by, system 100. RDBMS and SQL are known to those skilled in the art and thus are not further described herein.

User interface 120 may represent an interface module configured for bi-directionally communicating with computing devices 108 ... 110 via application level protocols suitable for web-based applications, mobile applications, email applications, messaging (e.g., video, audio, text, etc.) applications, and so on, and for generating appropriate graphical user interfaces suitable for displaying on computing devices 108 ... 110.

Settings 130 may be received from any of computing devices 108 ... 110 via user interface 120. Settings 130 may comprise user settings 131 and/or global settings 133. User settings 131 may refer to settings specific to a specific user of system 100, for example, a preference of a CDI specialist, the preference indicating a query score threshold for displaying CDI cases for review. Global settings 133 can include configuration parameters for condition models 160 and/or a system sensitivity rate that reflects a hospital's preferences with regards to false positives. In some cases, higher sensitivity (e.g., a greater likelihood of capturing query opportunities, but at an increased risk of false positives) may be desired. In other cases, a lowered sensitivity may be appropriate, as those skilled in the art can appreciate.

Parser 122 may be particularly configured for receiving and processing real-time medical/clinical data 103 and/or documentation 105 from hospital data source(s) 104 to identify entities of interest in the received data, extract them, and format/store them in appropriate data structures. Such entities of interest may represent features, factors, and/or medical concepts indicative of certain medical conditions. Additional details on hospital data source(s) 104 and parser 122 are provided below.

Documentation analysis by system 100 can including conducting a NLP process on patient data. NLP generally refers to a process by which a computer reads text and extracts meaningful information from it. In this disclosure, in the context of analyzing medical documentation, NLP refers to identifying which medical concepts have been documented (e.g., mentioned in a physician's note, a nurse's progress report, a lab report, etc.) in the patient data and what that documentation implies about those medical concepts (i.e., whether the documentation is stating that a patient does have a medical condition, does not have a medical condition, or may have a medical condition, etc.).

NLP engine 125 may be configured, according to some embodiments, for processing unstructured textual medical information contained in documentation 105 and, where applicable, hospital or clinical data 103. NLP engine 125 may operate to identify textual features or factors, such as instances of particular words, syntactical cues (e.g. certain words in the same sentence, etc.) which may then be inputted to parser 122 or ML systems to obtain a higher-level understanding of the text. NLP engine 125 can be implemented using any suitable NLP libraries or toolkits known in the art, such as Apache OpenNLP or NLTK 3.0.

According to some embodiments, condition engine 127 can be particularly configured for determining, based on data associated with a patient's case (e.g., during the patient's hospital visit) probabilities that: a.) the patient has a particular medical condition (such as, for example, hyponatremia, sepsis, heart failure, etc.), and b.) for each determined condition, the probability that the condition is accurately and/or correctly documented. Condition engine 127 can also be particularly configured for selecting which models (e.g., of models 160) to apply to the data associated with a particular case and application to generate these probabilities. Condition engine 127 may be implemented in hardware and/or software, or on a separate computer from other modules in the system.

CDI scoring engine 140 can be particularly configured for accessing one or more patient cases stored in data store 150 and evaluating such patient case(s) based on information currently available to system 100. The evaluation performed by CDI scoring engine 140 may comprise calling parser 122 to parse received real-time clinical data 103 and/or documentation 105 to determine entities of interest (e.g., features, factors, and/or medical concepts of certain medical condition(s)) in the received real-time medical data. CDI scoring engine 140 can also be particularly configured for calling condition engine 127 to determine which medical conditions are applicable to a patient, given the entities extracted from the received real-time data. CDI scoring engine 140 may operate to access data store 150 to retrieve additional patient information and build a data set (which includes the newly received real-time data) for the patient's current hospital visit. Based on the data set, CDI scoring engine 140 may operate to determine which condition models of condition models 160 are required for the determination of the patient's CDI score. For example, CDI scoring engine 140 may identify a diagnosis model and a documentation model for each condition for which the patient may have been diagnosed. Outputs from these condition models can be used to evaluate a patient case and generate a CDI score indicative of a CDI opportunity. The system-generated CDI scores may be stored in data store 150 and used by user interface 120 to generate an interface, which provides a list of patient cases, prioritized by the determined CDI scores, to a CDI specialist. Details and examples of CDI scoring can be found in U.S. patent application Ser. No. 15/349,679, filed Nov. 11, 2016, entitled "HIGH FIDELITY CLINICAL DOCUMENTATION IMPROVEMENT (CDI) SMART SCORING SYSTEMS AND METHODS," which is incorporated by reference herein.

Computing devices 108 may comprise mobile devices, such as cellular telephones, smartphones, tablet computers, laptop computers, personal digital assistants (PDAs), and the like, that run on various mobile operating systems such as iOS, Android, Windows Mobile, WebOS, BlackBerry OS, Palm OS, etc. Computing devices 110 may include wired computers such as desktop computers and/or wireless computers such as laptop computers that run on various operating systems such as OS X, Microsoft Windows, OpenVMS, VM, Solaris, and Linux, etc.

As a non-limiting example, each of computing devices 108 ... 110 may include a central processing unit ("CPU"), read-only memory ("ROM"), random access memory ("RAM"), a hard drive ("HD") or any other types of non-transitory storage memory, and input/output ("I/O") device(s). The I/O devices can include a keyboard, monitor, printer, electronic pointing device (e.g., a mouse, trackball, stylus, touch pad or screen, digitizer, microphone, etc.), or the like.

As discussed above, system 100 may be embodied on a single or multiple server machine(s). Each such server machine may include CPU, ROM, RAM, HD, and I/O devices similar to those described above. Likewise, hospital data source(s) 104 may be one or more computing devices which include a CPU, ROM, RAM, HD, and I/O devices similar to those described above.

Although a single hospital data source 104 is shown in FIG. 1, skilled artisans appreciate that hospital data source 104 may represent a single source or multiple sources associated with a particular hospital system or healthcare facility. Furthermore, multiple hospital systems and/or healthcare facilities may be communicatively connected (via appropriate hardware, software, and network technologies) to system 100 and provide real-time medical data for use by system 100, including clinical documentation generated at a hospital.

As used herein, the term hospital refers to any healthcare facility, clinic, hospital, doctor's office, etc., and the term clinical documentation refers to healthcare information that documents a patient's condition and the care given to the patient. As will be further described below, real-time medical data from hospital data source 104 may be provided to system 100 via one or more feeds such as HL7 (Health Level 7) feeds. The HL7 feed may be provided to system 100 via an HL7 gateway 129. In some embodiments, HL7 gateway 129 may be integral to, or physically separate from system 100. The HL7 protocol is an open source protocol promulgated by Health Level Seven International, Ann Arbor, Mich., that defines how various healthcare facilities can communicate with each other. It is noted, however, that feeds via other protocols, such as the File Transfer Protocol (FTP) or Hypertext Transport Protocol (HTTP), are also possible.

Embodiments disclosed herein are capable of tapping into all available, disparate data streams. Example feeds may include, but are not limited to, admission-discharge-transfer (ADT) feeds (i.e., procedural or administrative information relating to each patient's stay at a facility); any orders (e.g., procedures/tests ordered for a specific patient); any lab results (e.g., from blood tests, etc.); any radiology results (e.g., results of x-rays, magnetic resonant imaging (MRI), computer-assisted tomography (CAT) scans, and the like); any results of cardiology exams; any prescriptions/pharmacy orders; any actual pharmaceutical/drug administration; any billing and coding data; and so on. Skilled artisans appreciate that HL7 ADT messages carry patient demographic information for HL7 communications, but also provide important information about trigger events (e.g., patient admissions, discharges, transfers, registrations, etc.). Segments in an ADT message may include a Patient Identification (PID) segment, a Patient Visit (PV1) segment, and occasionally an Insurance (IN1) segment. ADT messages are common in HL7 processing and are widely used in the healthcare field.

In some embodiments, system 100 may receive, at the minimum, ADT and lab results data feeds. Some data feeds can be optional. In some embodiments, system 100 may receive at least some of the following data feeds:

Lab Orders
Microbiology Results
Pathology Results
Pharmacy Orders
Radiology Orders
Radiology Results
Cardiology Results
Vital Signs
Physician Documentation The Physician Documentation data feed can include various types of documentation pertaining to patient care, for instance, history and physical (referred to as H&P), admission reports, daily progress notes (e.g., physician notes, nursing notes, etc. which can reference other orders and/or reports such as radiology orders, pharmacy orders, radiology results, conditions, results of other conditions, discharge reports, etc.).

An exemplary HL7 message is shown below. This HL7 message represents the results of a complete blood count (CBC) lab procedure:

```
MSH|^~\&|LAB|IODINE|||201606121531||ORU^R01|ID12345|P|2.3|||||
PID|1|MRN12345|ACCT98765|1221|SMITH^BOB||19850608|M|||12345 MAIN
ST^AUSTIN^TX^^78701|||||||ACCT98765|123-45-6789||||||||
PV1|1|I|FACILITY.1||||DRID12345^JOHNSON^SALLY||NONE^None|||||||N|
|REF||IN|||||||||||||||||||CMC||FACILITY.1|||201606101110||||||
ORC|||||||||||||||||
OBR|1|ORDER123^LAB|ORDER123^LAB^ALTORDER5678|CBC^LAB
CBC|||2016061
11212||||||||201606111244||DRID12345^JOHNSON^SALLY|||||||||LAB|F||^
^^^R|||||||
OBX|1|ST|WBC^WBC^L|8.7|K/uL|3.6-10.8|N||F|||201606111244||
OBX|2|ST|RBC^LAB RBC^L|1|4.83|M/uL|4.2-
5.4|N||A^S|F|||201606111244||
OBX|3|ST|HGB^Hemoglobin^L|1|13.6|g/dL|12.0-
16.0|N||A^S|F|||201606111244||
OBX|4|ST|HCT^Hematocrit^L|1|40.7|%|37-
47|N||A^S|F|||201606111244||
OBX|5|ST|PLT^Platelet Count^L|1|390|K/uL|150-
400|N||A^S|F|||201606111244||
OBX|6|ST|MPV^MPV^L|1|10.2|fL|7.4-10.4|N||A^S|F|||201606111244||
OBX|7|ST|GRP^Gran % (Auto)^L|1|74.7|%|42-
72|H||A^S|F|||201606111244||
OBX|8|ST|LYP^Lymph % (Auto)^L|1|18.9|%|20.5-
51.1|L||A^S|F|||201606111244||
OBX|9|ST|MIDP^Mid Range %
(Auto)^L|1|6.4|%||N||A^S|F|||201606111244||
OBX|10|ST|GRA^Gran # (Auto)^L|1|6.5|K/uL|1.8-
7.7|N||A^S|F|||201606111244||
OBX|11|ST|LYA^Lymph # (Auto)^L|1|1.6|K/uL|1.0-
4.8|N||A^S|F|||201606111244||
OBX|12|ST|MIDA^Mid Range #
(Auto)^L|1|0.6|K/uL||N||A^S|F|||201606111244
```

The first line—the MSH segment—indicates that this is a result (as indicated by "ORU-R01").

The 2nd line—the PID (patient identifier) segment—provides identifying information about the patient. In this example, the patient's name is Bob Smith; he lives at 12345 Main St.; his medical record number is MRN12345; and his account (case) number is ACCT98765.

The 3rd line—the PV1 (patient visit) segment—provides status information about the patient's current visit. In this example, the message segment indicates that he is an inpatient who was admitted on Jun. 10, 2016 at 11:10 a.m.

The 4th line—the OBR segment—provides information about the order that was previously placed that caused this lab procedure to be performed. In this example, the message segment indicates that Dr. Sally Johnson ordered the procedure with id "CBC" and named "LAB CBC" at 12:12 p.m. on Jun. 11, 2016.

Each of the remaining lines contains a single result. For example:

```
OBX|1|ST|WBC^WBC^L|8.7|K/uL|3.6-10.8|N||F|||20160611012441||
OBX = indicates that this line contains a result
1 = indicates that this is the first result line returned for the
order
ST = indicates that the result contains a simple string value
WBC^WBC LAB^L = indicates that the result is a "WBC LAB" result
with an ID of "WBC"
8.7 = This is the actual numerical result
K/uL = These are the units of measure for the result
3.6-10.8 = This is the reference range for this particular result
N = This is where abnormality flags would be. N indicates
"normal"
F = Final status
```

In some embodiments, system 100 is always ready to receive these data feeds, 24 hours a day, seven days a week. In some embodiments, using an HL7 feed, a stream of data may be updated when an event at a particular hospital or source is updated. As discussed above, the updated raw data may be stored in a hospital data database represented by hospital data 170 in FIG. 1. Parser 122 may parse the new information, and output entities of interest found in clinical data 103, documentation 105, and/or hospital data 170.

In some embodiments, each piece of data is processed in near-real-time. As a specific example, most data can be processed within 10 minutes, or less, of receipt by system 100. Environmental and configuration settings can sometimes extend processing times. In some embodiments, each time a patient case receives new data, its CDI score is updated.

7 The CDI score can be a discrete numerical value representing a significance or level of opportunity for improvement for clinical documentation associated with a patient in a hospital. For example, a high CDI score may indicate that a patient has a medical condition that is reflected in their clinical data, but that is not correctly or accurately documented. A CDI score maybe weighted by the significance (which may be expressed, for example, as a combination of clinical and financial concerns) of the under- or over-documented and/or over- or under-diagnosed patient medical condition. For instance, the system may determine that the clinical data of a particular patient admitted for treatment of sunburn reflects an undocumented dehydration (i.e., the documentation associated with the same patient does not contain dehydration as a documented condition). In some embodiments, the system may utilize a weighting scheme to ensure that the undocumented dehydration is a condition highly correlated to sunburn, as opposed to life-threatening sepsis, of which dehydration is also a condition.

CDI specialists have a finite amount of time and often cannot get to all initial reviews and re-reviews of patient charts for CDI purposes. The CDI scoring technology described in the above-referenced U.S. patent application Ser. No. 15/349,679 can streamline a CDI specialist's task in determining which patient charts to review and enable them to make an informed decision as to how they could best improve the accuracy of the given clinical documentation. For example, a user interface 120 may operate to generate, in real-time, a list of patient cases prioritized by the determined CDI score. The prioritization provided by the system can enable them to focus on cases with the most impact when they perform CDI reviews, thereby improving the efficiency and effectiveness of their work. In turn, such an improvement could provide a positive impact on the hospital's insurance reimbursement rates, healthcare quality ranking, etc.

While the data feeds provide the system with massive amounts of patient data, the patient data is often incomplete and/or inaccurate. One reason is that medical documentation is often manually entered and/or created by healthcare personnel and not automatically generated.

For example, the system may receive real-time medical data concerning a patient. Although the patient's attending physician(s) should have specified whether the patient is actually obese or overweight (if those labels apply), this documentation is commonly missed by physicians. To address this issue, the system may be configured to recognize entities of interest such as body mass index (BMI) and parse the real-time medical data to extract the BMI of the patient. The system may determine (e.g., by consulting an indicator table storing indicator information that has been vetted by subject matter experts) that the BMI for the patient is high. Since a high BMI may be an indicator for obesity, the system may identify obesity as a medical concept associated with the patient and store this concept in the patient's case file or record in data store 150, even though this medical concept was not contained in the real-time medical data received by the system. The system may evaluate the patient's case, which now includes the newly determined medical concept, and determine that the current clinical documentation is missing information on obesity. In this way, the system can identify missing and/or inaccurate information in a patient's case and generate a CDI score such as a score of 0-100 that represents a significance or level of improvement. For example, a score of 100 may indicate that this patient's case is extremely likely to need a CDI review and the CDI review may result in a significant impact in improving the quality of the clinical documentation for this case.

By presenting a CDI specialist with a list of patient cases ranked according to the CDI score, the CDI specialist can easily prioritize which patient charts to review and when to initiate a query to resolve an under- or over-documentation issue. In some cases, input from a CDI specialist may also affect, both in the short term and in the long term, how the system scores patient cases for CDI specialist review.

(i) Short Term Impact—once a CDI specialist has reviewed a patient's chart and has taken the necessary steps to ensure that the clinical documentation for that patient is accurate (at the time the CDI review is complete), then, in some embodiments, the CDI score associated with the particular patient case can be updated to be (or reset to) zero for the time being. This CDI score may be updated again when new information about the patient's care is received and the patient's case is re-evaluated by the system, at which time, the system may generate a new CDI score indicating that a re-review may be needed for the patient's case to further improve clinical documentation on the patient's care.

(ii) Long Term Impact—a CDI specialist may indicate to the system (e.g., via a graphical user interface generated by user interface 120 of system 100) which queries resulted in actual improvement to clinical documentation. In this way, the system can learn and/or gain knowledge on what the global "success rate" of each query is relative to the CDI scoring process, and can globally adjust the weight of the CDI in the CDI scoring algorithm as needed.

While system 100 can timely identify which patient's case is extremely likely to need a CDI review, it lacks the ability to quantitatively prove that a patient's case is sufficiently documented. As discussed above, sometimes the mere documentation of a condition in the patient's records is not enough. For example, in some cases, some payers or government regulation (e.g., Medicare) for clinical documentation may require, in addition to documenting the existence of a condition in a patient's records, that the condition is documented at various time points over the course of a patient's stay (i.e., no DDOs in the patient's records).

Preventing or detecting DDOs can be technically challenging at least because the amount of patient data that needs to be processed can be staggering. As described above, a real-time medical communication system such as system 100 is always ready to receive multiple data feeds, 24 hours a day, seven days a week. At any given time, a hospital may have tens and thousands of patient visits. Each patient can have many, many pieces of data collected over the course of their visit or stay, from admission to discharge (e.g., admission date, time, patient identifier, length of stay, admission condition, admission notes, type and time of medication administered, attending physician, on-call physician, head nurse, assistant nurse, patient temperature, patient blood pressure, patient white blood cell count, test orders, test results, the number of times the patient is feverish, progress reports, vital signs, medication orders, etc.).

Another technical challenge is how to program a computer to look for things (in this case, documentation of a patient's condition) that are not there in the patient's clinical documentation and/or that were present at some time during the patient's visit but disappeared afterwards. While CDI specialists can, to a certain extent, utilize human intuition and experiences to potentially spot DDOs and identify what is missing in the patient's clinical documentation, it is an unreliable, error-prone, and time-consuming process that often cannot be reproduced, duplicated, or performed in real time.

Figure 2:
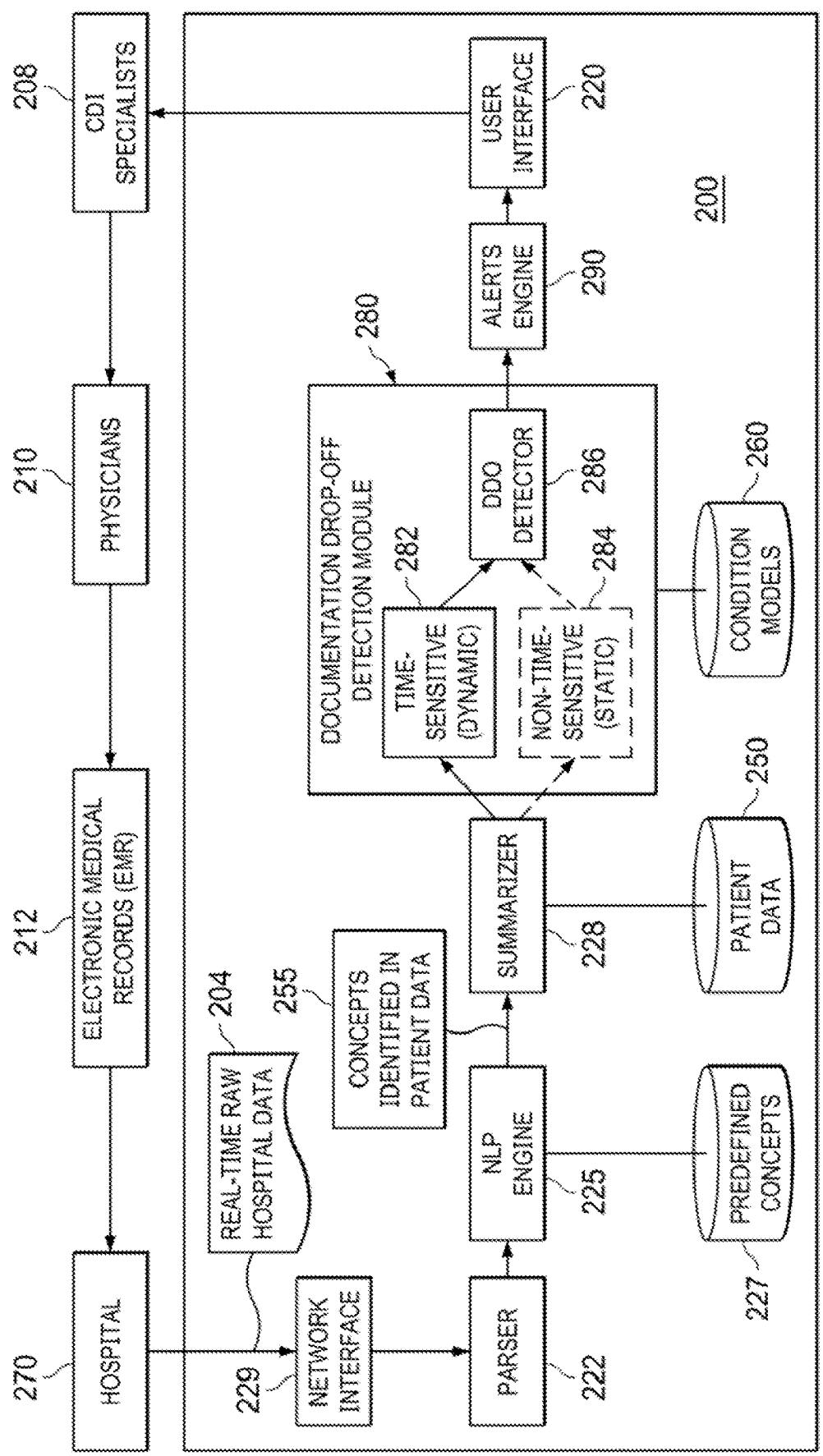
FIG. 2 depicts a diagrammatic representation of an example of a real-time medical communication system with a documentation drop-off detection module according to some embodiments.

To this end, embodiments disclosed herein provide a new real-time medical communication system with a DDO detection module for timely identifying and detecting DDOs in real-time medical data. FIG. 2 depicts real-time medical communication system 200 having system components such as parser 222, NLP engine 225, condition models 260, and user interface 220 similar to those of system 100 (e.g., parser 122, NLP engine 125, condition models 160, and user interface 120, respectively). Additionally, system 200 includes DDO detection module 280 operating downstream from summarizer 228 and upstream from alerts engine 290.

Figure 3:
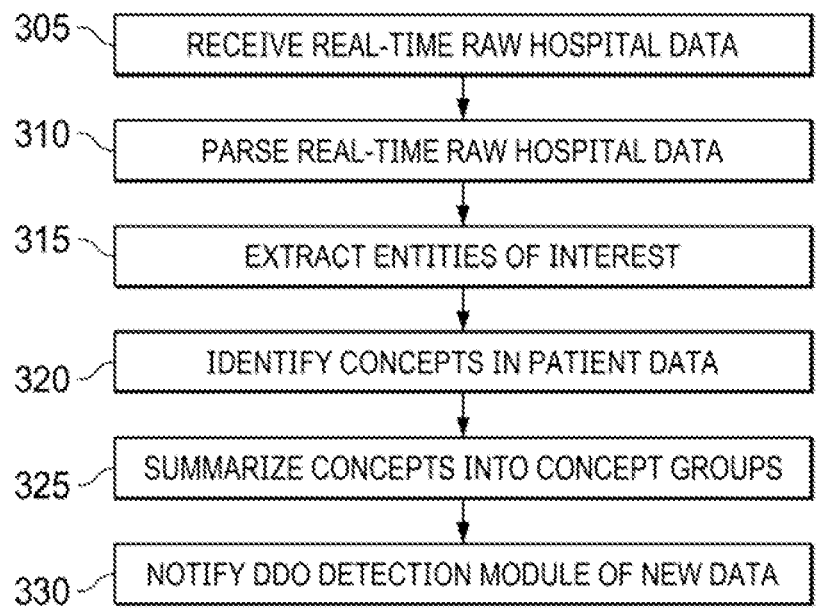
FIG. 3 depicts a flow chart illustrating an example of a method for processing real-time medical data for input to a documentation drop-offs module according to some embodiments.

Referring to FIG. 3, in some embodiments, data processing process 300 can including receiving real-time raw hospital data 204 (which can include messages in the HL7 format discussed above, each message for a patient) from hospital 270 through network interface 229 (which, in one embodiment, can be part of an HL7 gateway) of system 200 (305). Parser 222 may operate to parse real-time raw hospital data 204 (310) to identify entities of interest (e.g., admission, transfer, test orders, test results, patient demographic information, payer information, medication orders, medication administrations, hospital service line/department, radiology orders, radiology results, cultures, any previous diagnoses, and any documentation associated therewith, for instance, a patient's BMI, vital signs such as heart rate and body temperature, white blood cell count, blood pressure, blood test result, urine test result, history-and-physical notes, progress notes, physician consults, specialty notes such as physical therapy notes, pharmacy notes, nurses notes, emergency department notes, and/or dietician notes, etc.). Parser 222 may then extract and output the entities of interest (315). The extracted entities of interest can be stored e.g., in a data store accessible by NLP engine 225) and/or communicated to NLP engine 225.

In some embodiments, NLP engine 225 may take the extracted entities of interest from parser 222 as input and operate to identify terms (e.g., names, phrases, etc.) in the extracted entities of interest that may be categorized into medical concepts ("concepts") 255 (320). In some embodiments, NLP engine 225 may do so by comparing terms in the extracted entities of interest with predefined concepts stored in data store 227. Such concepts generally correspond to diseases, symptoms, parts of the body, medications, procedures, treatments, and so on. For example, "acute renal failure," "acute kidney injury," etc. can be specifically identified, coded into the NLP engine, and mapped to the same concept of "kidney disease."

In some embodiments, concepts utilized by the NLP engine may follow the Unified Medical Language System (UMLS) provided by the National Institutes of Health (NIH). The UMLS is a set of files and software that brings together many health and biomedical vocabularies and standards to enable interoperability between computer systems. The UMLS can be used to enhance or develop applications, such as electronic health records, classification tools, dictionaries, and language translators.

In this case, the UMLS (or, specifically, the Metathesaurus) is used to code the NLP engine so that synonymous terms can be grouped or otherwise mapped into concepts. The Metathesaurus is organized by concept and currently has over one million biomedical concepts and 5 million concept names. Each concept has specific attributes defining its meaning and is linked to the corresponding concept names in the various source vocabularies. Relationships between the concepts are represented, including, for instance, hierarchical relationships, such as "is a" for subclasses and "is part of" for subunits, and associative relationships, such as "is caused by" or "in the literature often occurs close to" (the latter of which is derived from Medical Literature Analysis and Retrieval System Online, also known as Medline). The UMLS is known to those skilled in the art and thus is not further described here. Other types of medical classification systems providing diagnosis codes tracking diseases and health conditions (e.g., chronic diseases such as diabetes mellitus and heart disease, and infectious diseases such as norovirus and the flu) and procedure codes tracking interventions, treatments, and medications given may also be used.

Operationally, the NLP engine can determine whether any of the extracted entities of interest (e.g., specifically identified and coded medical terms) corresponds to any of the predefined concepts. The specific concepts used by the NLP engine may be stored as a list in a dictionary file (e.g., dictionary 410 shown in FIG. 4). Using the dictionary, the NLP engine can process the extracted entities of interest from the parser and categorize them into appropriate concept(s). One way this categorization can be done is through tagging.

There may be a dozen different colloquial ways healthcare professionals talk about a patient's diagnosis (e.g., "systolic heart failure"). If the NLP engine finds, for instance, using the dictionary, any mentions of any of those mentions relating to systolic heart failure, the NLP engine can tag each of them with the concept "systolic heart failure." Likewise, there could be a set of terms that the NLP engine will tag "diastolic heart failure." For terms (or mentions) like "heart failure" or "HF" where "systolic heart failure" or "diastolic heart failure" is not explicitly mentioned or used, the NLP engine can tag them with "unspecified heart failure."

Figure 4:
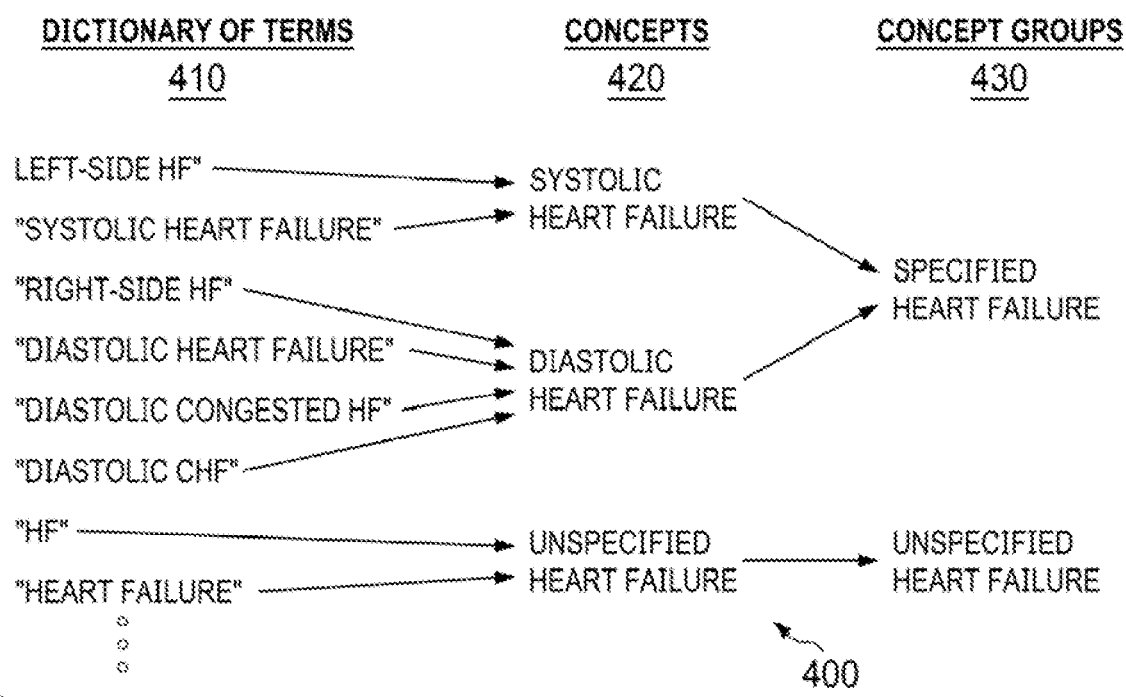
FIG. 4 depicts a diagrammatic representation of an ontology implemented by a real-time medical communication system according to some embodiments.

For example, suppose the parser has extracted "heart failure" and "HF" as entities of interest. As illustrated in FIG. 4, "heart failure" and "HF" are terms in dictionary 410, both of which are associated with one of predefined concepts 420: "unspecified heart failure." Thus, in this example, the extracted entities of interest "heart failure" and "HF" are tagged or otherwise associated with the concept "unspecified heart failure." Concepts thus identified in real time are patient-specific and each patient can have many concepts. In some embodiments, concepts identified by the NLP engine can be automatically summarized (e.g., by summarizer 228) into concept groups (e.g., concept groups 430).

Summarizer 228 can implement a proprietary ontology (e.g., ontology 400 shown in FIG. 4) that identifies fine-grained concepts as being analogous to the same (internally-defined) medical condition. This is an additional feature of system 200 because some medical diagnoses are not applicable for medical coding purposes. Implementing this ontology, summarizer 228 is operable to identify non-applicable concepts that are relevant to applicable concepts and group them together into concept groups 430 for further processing by DDO detection module 280 (325).

For example, heart failure—"unspecified heart failure" is unjustified heart failure. It is considered as not relevant because Medicare does not recognize it for reimbursement. However, systolic heart failure and acute heart failure could be combined into acute systolic feat failure. In this example, the systolic and acute types of heart failure are relevant for DDO detection, while unspecified heart failure is not.

The summarizer can filter out non-relevant terms. These terms are summarized so that they can be correctly coded (for medical coding purposes such as for reimbursement by Medicare). The combination of concepts represents a higher level of complexity (and thus are reimbursed at different rates). In the example of FIG. 4, the summarizer can combine "systolic heart failure" and "diastolic heart failure" into concept group "specified heart failure," in contrast to "unspecified heart failure." As another example, deep vein thrombosis (DVT) for the right leg and DVT for the left leg can be grouped into one concept group, DVT. In this way, summarizer 228 can operate to combine different concepts into groups of similar or related concepts or combine several concepts mentioned in a time frame as a concept group. In some embodiments, outputs from summarizer 228 can include summarized concept groups per patient.

In some embodiments, summarizer 228 can store, in data store 250 for each patient, summarized concept groups. In some embodiments, summarizer 228 can notify DDO detection module 280 that patient data in data store 250 have been updated (330). Although NLP engine 225 and summarizer 228 are shown in FIG. 2 as two modules, in some embodiments, they can be implemented as a single module.

In some embodiments, DDO detection module 280 is configured for continuously monitoring and determining whether a DDO has occurred in the patient data. To be considered sufficiently documented, a patient's stay (or visit) should be documented every day. The lack of documentation of a previously mentioned condition of the patient during a timeframe (e.g., 36 hours) can be considered as an indication that a DDO likely has occurred.

Documentation of a patient usually begins when a patient comes to a hospital. An admission team will fill out the history of the patient (e.g., H&P) and produce an admission report. If the patient comes in through the emergency department, there will be some kind of emergency notes that describe what happened there. Once the patient is admitted to the hospital, there are daily progress notes, which can include a physician's notes documenting the patient's conditions that the physician is responsible for, what the physician is doing about it, etc. Thus, standard documents that may be produced by healthcare professionals during a patient's stay can include H&P, emergency notes, admission report, notes taken after admission (e.g., daily progress notes), discharge report, etc.

Suppose that, for the first couple of days, the patient's primary doctor keeps writing down and mentioning sepsis, what he's doing to treat it, what the patient's symptoms are, etc. But on day 3, day 4, and on, he does not mention sepsis again or any ongoing process concerning sepsis in his physician notes. At the end of the hospital stay, there's a discharge report, which also does not mention sepsis. A DDO scenario likely has occurred in this case. Because of this, a coder is unlikely to identify sepsis as a condition that the patient had and was treated during his stay.

To identify a DDO scenario, however, can be extremely challenging. Generally, a computer can be provided with input data and programmed to identify what is in the input data and/or generate additional data from the input data. However, the computer has no way of knowing, on its own, that certain information is missing in the input data—it cannot know what it does not know. Complicating the matter is the amounts of documents produced by different people who may describe a patient's care in different ways, for instance, using different words, terms, and phrases. From this perspective, there are at least two main problems: how to determine whether a condition of the patient was documented during the patient's stay (e.g., between admission and discharge) and whether the condition was documented sufficiently during the same period.

To solve these and other problems, DDO detection module 280 can be particularly programmed with a non-time-sensitive component and a time-sensitive component. The non-time-sensitive component can implement non-time-sensitive ML models trained to determine, on a per condition basis, whether a condition of the patient was documented during the patient's stay and output a binary answer—"yes" indicating that a condition was documented or "no" indicating that a condition was not documented. This output is static and is not affected by time and thus is referred to herein as static, non-time-sensitive. The time-sensitive component can implement time-sensitive ML models trained to determine a likelihood (e.g., a probability) that a DDO for a condition has occurred during the patient's stay. This determination can change over time and thus is referred to herein as dynamic, time-sensitive.

In some embodiments, DDO detection module 280 can include time-sensitive component 282, that implements dynamic, time-sensitive ML models, and non-time-sensitive component 284, that implements static non-time-sensitive ML models. DDO detection module 280 can further include DDO detector 286 which, in some embodiments, can process outcomes from the models (e.g., 78% yes and 22% no for a concept or concept group) and determine, based on predefined thresholds, whether to trigger a DDO alert. If so, DDO detector 286 can notify alerts engine 290 which, in turn, can start a process to generate a DDO alert for user interface 220.

In some embodiments, inputs to time-sensitive component 282 and non-time-sensitive component 284 can include model variables (e.g., admission time, patient ID, length of stay, admission condition, patient temperature, white blood cell count, number of times the patient is feverish in the documented period, etc.). In some embodiments, time-sensitive component 282 may include a DL library and, for each condition in the condition models defined in the system (e.g., condition models stored in data store 260), a time-sensitive ML model such as a DL model particularly trained (explained below with reference to FIG. 3) to determine whether the condition is currently (within a configurable time period such as an hour, a day, etc.) sufficiently documented in a patient's record with regard to the patient's stay (e.g., at the hospital, healthcare facility, etc.).

An example of a DL library can be an open-source, distributed, DL library called "Deep Learning for Java" or "DeepLearning4J" available from deeplearning4j.org. DeepLearning4J, which allows the creation of custom layers, is known to those skilled in the art and thus is not further described herein. Such a DL library is used because recurrent neural networks (RNN) can exhibit the temporal dynamic behavior for a time sequence. A recurrent neural network is a class of artificial neural network where connections between nodes form a directed graph along a sequence. This allows it to exhibit temporal dynamic behavior for a time sequence. Unlike feedforward neural networks, RNNs can use their internal state to process sequences of inputs.

In this case, inputs to time-sensitive component 282 include timestamps and concept groups for each patient in the patient data. A goal here is to obtain a time-series with a binary answer or indicator for each concept group. More specifically, at each time stamp, time-sensitive component 282 is operable to determine whether a group of concepts corresponding to a medical condition was mentioned (i.e., documented in the patient's record) during that time. This is done for each condition of a list of conditions modeled in system 200 (e.g., condition models 260). Based on this evaluation, time-sensitive component 282 can produce a time-series of yes's and no's (with respect to concept groups) for each day (or timestamp) during the patient's stay.

For example, suppose a patient "John Doe" comes into a hospital. Time-sensitive component 282 is operable to identify, from patient data 250, that, on day 1, John Doe was documented (e.g., in an admission report, H&P, etc.) with "HF," "unspecified HF," and "hyponatremia." Based on this information, time-sensitive component 282 can generate a time series for John Doe on day 1 as follows:

day 1—"no" to the first concept group "specified heart failure"; "yes" to the second concept group "hyponatremia"; . . . "no" to the nth concept group.

In this example, the entities of interest "HF" and "unspecified HF" are ignored (e.g., not in the input time-series data to time-sensitive component 282) because the concept group to which they belong ("unspecified heart failure") is not considered by system 200 as relevant for medical coding purposes.

Suppose on day 2, John Doe's doctor wrote in his physician note "left-side HF." In this case, "left-side HF" is categorized (e.g., first tagged by NLP engine 225 as concept 420 and then grouped by summarizer 228 into concept group 430) as "specified heart failure," which is considered by system 200 as relevant for medical coding purposes. Thus, time-sensitive component 282 can generate a time series for John Doe on day 2 as follows:

day 2—"yes" to the first concept group "specified heart failure"; "yes" to the second concept group "hyponatremia"; . . . "no" to the nth concept group.

During John Doe's stay at the hospital, time-sensitive component 282 is operable to generate, on the fly, a time-series of binary answers (e.g., yes's and no's) each day. The number of binary answers corresponds with the number of concept groups that time-sensitive component 282 is configured to process. Suppose there are n (e.g., n=100) concept groups, the time-series on day 1 can have a total of n binary answers: "no, yes, yes, no, no, no, . . . " and, on day 2, it can again have a total of n binary answers: "yes, yes, no, no, no, no, . . . " In this example, documentation for the third concept group is dropped.

As discussed above, summarizer outputs can be stored in a database (e.g., data store 250). The summarizer outputs are stored in the database on a per-patient basis. In this way, each patient case can have a timestamp, a visit ID, a patient ID, extracted concepts, determined concept groups, details of the documents, type of documents (e.g., discharge reports, who the author was, daily progress notes, etc.). DDO detection module 280 can access summarizer outputs and perform DDO evaluation on a continuing basis and/or whenever new data is received. As discussed above, summarizer 228 may notify DDO detection module 280 that new patient data has arrived in data store 250. In response, DDO detection module 280 can pull what it needs from data store 250 (e.g., patient ID, visit ID, timestamp, concept groups, etc.). DDO detection module 280 can pull a newly updated patient record based on a predefined list of group concepts that DDO detection module 280 was programmed to look for. For example, if a patient record does not contain any of the predefined concept groups, DDO detection module 280 may not pull that patient record as there is no need for DDO detection module 280 to process that patient record. For each patient record pulled, DDO detection module 280 is operable to create a time-series of when grouped concepts are documented through that patient's stay, up until now, in an accumulative manner.

In some embodiments, the patient record may also include semantic attributes about each concept. Such semantic attributes can facilitate the DDO determination. For example, suppose a patient record inputted to time-sensitive component 282 include the following data points:

day 1, "likely HF" (which leads to a "no" to "specified heart failure")

day 2, "possibly systolic HF" (which leads to a "yes" to "specified heart failure")

days 3, 4, "systolic HF" (which leads to a "yes" to "specified heart failure")

day 5, "ruled out systolic HF" (which leads to a "no" to "specified heart failure")

In this case, the semantic attribute "ruled out" indicates that a DDO for the concept group "specified heart failure" did not occur. More specifically, at the beginning, the doctor is evaluating the patient and thinks that it's probably systolic heart failure. He talks about heart failure for the next couple of days. Then he ruled out heart failure altogether. The fact that he didn't talk about heart failure any more is not a DDO. Rather, the patient was cleared of the earlier diagnosis of a "likely" heart failure.

To accomplish this, the NLP engine first recognizes that "HF" was modified by "likely" and extracts "likely" as a semantic attribute for the concept "H F." For each concept that it identifies for a patient, the NLP engine can store, in the patient's file or record, a number of attributes: negated, historic mentions (with respect to the patient's history), family history, uncertain (e.g., "likely"), conditional, surgical, etc. These attributes are stored in the database and retrieved by time-sensitive component 282 along with concept groups. That is, rather than processing a series of time point specifying "unspecified HF," "systolic HF," etc., time-sensitive component 282 processes and evaluates "possible unspecified HF," "uncertain systolic HF," "definite systolic HF," "negated systolic HF," etc. Suppose a concept group in the time-series is never "negated." For instance, for a while, the documents mention words and phrases like "uncertain", "definitely there," etc. concerning heart failure. Then, the documents stopped mentioning heart failure. In this case, it is likely that a DOO has occurred.

The time-series data that time-sensitive component 282 generated for each patient can be provided as input to time-sensitive DL models, each of which is trained to determine a likelihood that a concept group (e.g., a target medical condition or "condition") is sufficiently documented.

Figures 5, 6:
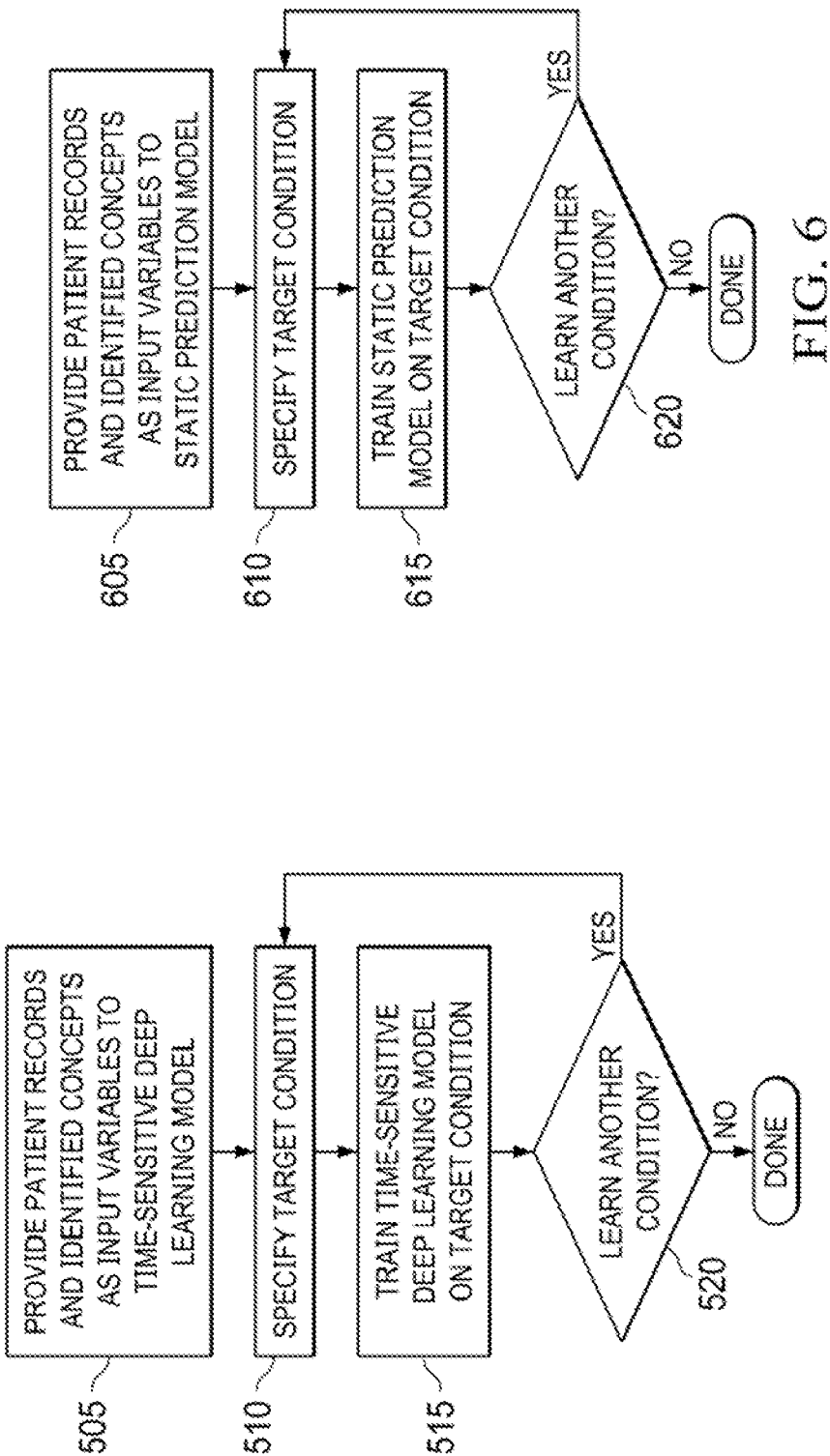
FIG. 5 depicts a flow chart illustrating an example of a method for training time-sensitive deep learning models according to some embodiments.
FIG. 6 depicts a flow chart illustrating an example of a method for training static prediction models according to some embodiments.

FIG. 5 depicts a flow chart illustrating an example of a method for training time-sensitive DL models according to some embodiments. In this example, the time-sensitive DL models are trained (e.g., through supervised learning) using actual and/or synthetic historical time-series patient data as the training data. The training data may contain a huge amount of data (e.g., millions of patient visits in the past, tens or hundreds of thousands of patient records, etc.) in which conditions of each patient are clearly identified in the patient records (e.g., a temporal pattern of yes's and no's of a concept group during a patient's stay) so that it is known to the machine under training (e.g., time-sensitive component 282) what condition each patient has and does not have documented in their patient data and what a corresponding temporal pattern (which can be derived from the historical time-series data) looks like (505).

The machine (e.g., time-sensitive (dynamic) component 282) running the time-sensitive DL models is trained on a per condition basis. This means that the machine processes the input training data for each specified target condition (510).

For example, suppose the training target condition is "sepsis," the machine may operate to examine each patient record in the training data and learn to recognize a pattern of how "sepsis" is documented during each patient's stay. This learning process can be iterative and fine-tuned to increase accuracy. This learning process can also be continuous so that processed new patient records can be used to further train the machine and improve the machine's performance over time.

When all patient records in the training data have been processed, the machine may proceed to learn the next condition or terminate when all conditions corresponding to condition models 260 have been run (520). Once trained, the machine can, at runtime, take an input time-series and determine, based on historical time-series that are similar to this input, a probability on whether a target condition is sufficiently documented during a patient's stay (e.g., 80% chance that this condition is "coded out," for instance, for Medicare reimbursement).

As the above example illustrates, by running time-sensitive DL models trained to process a set of conditions and, for each condition, determine whether it is sufficiently documented during a patient's stay, the machine running time-sensitive component 282 can identify the presence of a condition in a patient's documentation. However, this means that all time-sensitive DL models would be run. For increased efficiency, in some embodiments, DDO detection module 280 may run non-time-sensitive models to detect the presence of a condition or conditions in a patient's time-series data and run time-sensitive DL models to process the condition(s). In this way, time-sensitive component 282 can be specialized in determining whether a target condition is sufficiently documented during a patient's stay.

The machine running the non-time-sensitive models (e.g., non-time-sensitive (static) component 284) can be trained using the same training data described above. That is, for each condition in the condition models (e.g., condition models 160) defined in the system, non-time-sensitive component 284 may include a static ML model particularly trained to determine whether a condition is documented in a patient's record during a patient's stay. In some embodiments, the static ML model may implement a gradient boosting machine (GBM). Gradient boosting is a ML technique that is highly customizable and that produces a data-driven static prediction model useful for solving classification problems.

FIG. 6 depicts a flow chart illustrating an example of a method for training static prediction models according to some embodiments. In this example, the static prediction models are trained on the same actual and/or synthetic patient data used to train the time-sensitive DL models (605). The machine (e.g., non-time-sensitive component 284) can process the input training data for each specified target condition (610). For example, the machine can be fed with historical records of patients who have sepsis documented, as well as of patients who do not have sepsis documented. The machine learns from such input data what concepts correspond to sepsis and what concepts do not and, thus, how to predict sepsis having been documented with an acceptable level of confidence (615). This learning process is repeated for each condition (e.g., pneumonia, heart failure, acute renal failure, DVT, and so on). When all patient records in the training data have been processed with respect to a target condition, the machine may proceed to learn the next condition or terminate when all conditions corresponding to condition models 260 have been run (620).

In this way, the machines can be trained to learn to identify, on the fly, patient conditions that have been documented in the incoming real-time medical data (utilizing the static prediction models) and determine whether any DDOs likely have occurred in any documented condition (utilizing the time-sensitive DL models). As skilled artisans can appreciate, a different set of patient data may be used as the test data to test the accuracy of each model. The results can then be used to fine tune and improve the models.

Each condition that has been modeled in the system can have both a trained time-sensitive (dynamic) model and a trained non-time-sensitive (static) model associated therewith. Once trained on a condition, each model can process new patient data and output a model confidence as to whether or not that condition has ever been documented for this patient (a static output) or whether that condition is currently sufficiently documented for the patient (a dynamic output). The model confidence indicates a likelihood or potential that the patient has the condition documented or is currently sufficiently documented the patient's stay, based in part on the real-time patient data provided by the hospital to system and processed, on the fly, by the system according to the system's internal ontology.

Returning to FIG. 2, in some embodiments, before runtime, a threshold can be defined for all conditions for use in determining whether a condition is ever documented for a patient's stay. Alternatively, thresholds can be defined on a per condition basis. Each model output is compared with an appropriate threshold to determine whether a patient should be coded for a particular condition. For example, an identified concept "DVT" for patient A may be inputted to a static prediction model of non-time-sensitive component 284 particularly trained for the condition of deep vein thrombosis. The static prediction model may operate to determine that there is a 71% likelihood that patient A has the condition of deep vein thrombosis documented. This output is compared with a predefined threshold of 70. In this example, since the model output exceeds the predefined threshold, system 200 may operate to determine that patient A indeed has the condition of DVT documented and, therefore, clinical documentation for patient A should be coded for DVT.

Compared with non-time-sensitive component 284 which is fed with data reflecting a patient's entire length of stay each time data 204 is pushed to system 200, data taken in a snapshot in time (e.g., one hour) is fed to time-sensitive component 282. In turn, time-sensitive component 282 is operable to determine, based on concepts identified in the snapshot in time, whether, for each condition identified by the associated static prediction model, the documentation of that condition is sufficient at the current point in time. Following the sepsis example, time-sensitive component 282 may operate to determine, for each hour of data received, whether patient A has sepsis sufficiently documented during that time period. The granularity level of time period can be configurable (e.g., every hour, every three-hour, every 12-hour, everyday, etc.).

In some embodiments, DDO detector 286 is operable to compare outputs from time-sensitive component 282 and non-time-sensitive component 284 and identify/detect any patient-specific condition that may be documented at some point in time in the clinical documentation, but not sufficiently documented over the course of the patient's stay (a DDO). DDO detector 286 may communicate a finding of a DDO to alerts engine 290. Alerts engine 290 may generate an alert or notification accordingly and communicate same to user(s) (e.g., CDI specialists 208) through user interface 220.

CDI specialist(s) 208 can inform or request the patient's attending physician or health care provider 210 to update the patient's electronic medical records (EMR) 212 at hospital 270 to remedy the DDO. As illustrated in FIG. 2, the updated EMR for the patient is entered into the hospital's system which sends it to system 200 (e.g., through the next push of real-time medical data 204). Parser 222 of system 200, in turn, can parse out updated EMR 212 for the patient from real-time medical data 204. The parsed outcome can then be processed by NLP engine 225 and/or summarizer 228 which then update the patient's data in data store 250 and notify DDO detection module 280 to recalculate the DDO potential for the patient's records, thereby completing the CDI loop. The patient's condition is now considered to be sufficiently documented and the DDO problem is prevented or eliminated.

Figure 7:
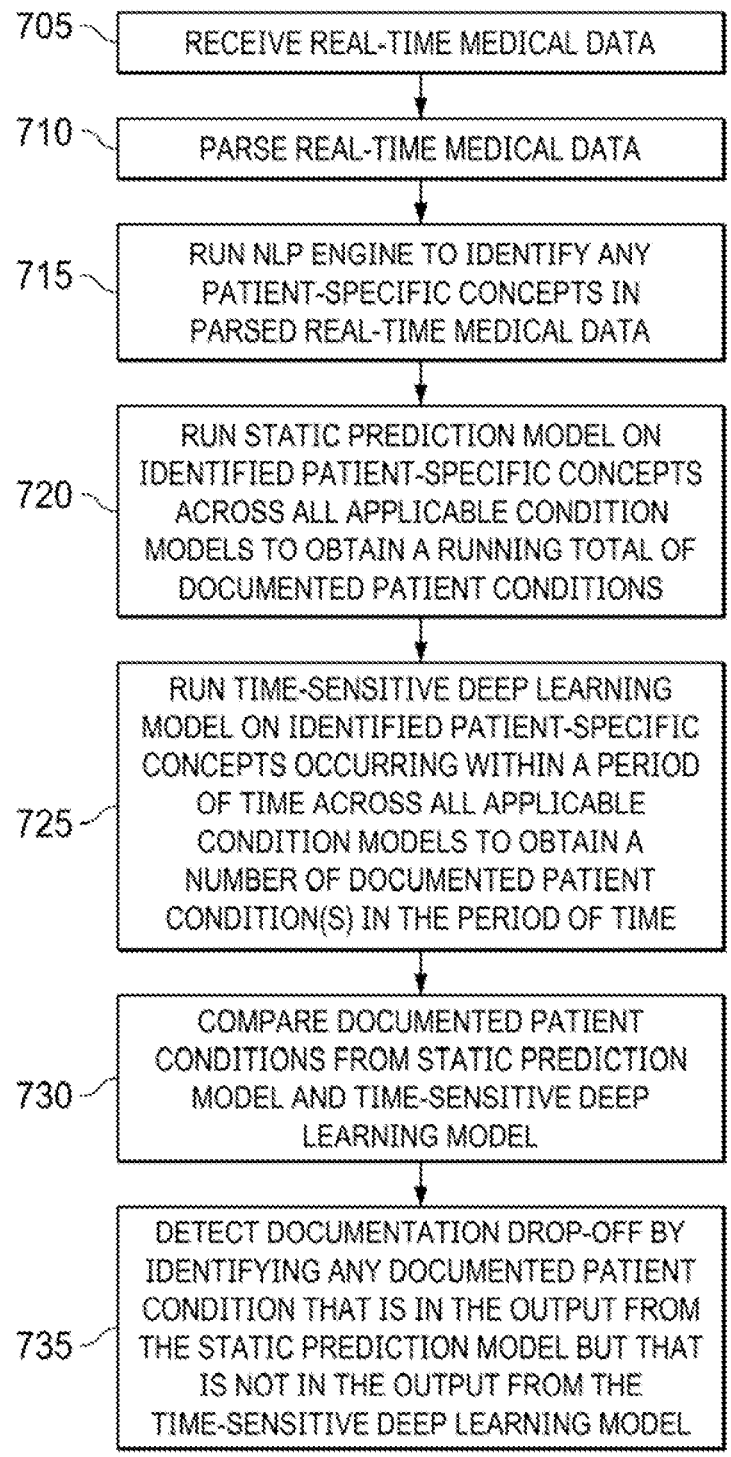
FIG. 7 depicts a flow chart illustrating an example of a method for detecting documentation drop-offs according to some embodiments.

The above-described process is illustrated in FIG. 7 which depicts a flow chart illustrating an example of a method for detecting DDOs according to some embodiments. As illustrated in FIG. 7, method 700 may comprise receiving real-time medical data (e.g., patient-specific HL7 messages) from a data source (e.g., a hospital system) (705) and parsing the received real-time medical data (710) to identify entities of interest (to a real-time medical communication system disclosed herein).

The extracted entities of interest are fed to an NLP engine. The NLP may operate to identify any patient-specific concepts using a dictionary containing a list of predefined concepts and texts representing such concepts (715). The same set of patient-specific concepts is provided as input to static prediction models (720) and time-sensitive models (725).

On a per condition basis, a static ML engine (e.g., non-time-sensitive 284) applies static prediction models to the patient-specific concepts across all the applicable conditions (as defined in the condition models by the underlying system) and generates an output containing a list of documented conditions that the patient likely has during the patient's stay. On a per condition basis, a time-sensitive ML engine (e.g., time-sensitive 282) applies time-sensitive DL models to the same set of patient-specific concepts across the documented conditions (or, alternatively, across all the applicable conditions) within a preconfigured timeframe (e.g., accumulatively, every time the patient's data is updated, from the patient's admission up until now). The time-sensitive ML engine generates an output containing a running total of documented conditions that the patient likely has sufficiently documented during the time period. The outputs from both engines are compared (e.g., by DDO detector 286) (730) to identify any condition that is identified by the static ML engine as having been documented during a patient's stay, but that is not identified by the time-sensitive ML engine as having been sufficiently documented during the time period (i.e., a DDO has occurred) (735).

The above-described process may be performed continuously until the patient is discharged. The discharge can be detected by system 200 through a HL7 status message that indicates that the patient is discharged. The status message may be extracted as an entity of interest and the NLP engine may be notified. The status message can be provided to the DDO detection module along to indicate that this is the last update to the patient.

At the last step of processing, a patient is associated with a list of conditions and each condition has an associated score indicating the likelihood that the condition is sufficiently documented. The DDO detection module may operate to compare model outputs on a per condition basis and identify what condition is documented according to the static prediction model associated with the condition, but not verified as sufficiently documented per the time-sensitive DL model associated with the condition. The non-verification means that an attending physician or healthcare provider for the patient has not written about the particular condition for the patient for a while. Accordingly, the system notifies the CDI nurse or specialist to ask the physician or healthcare provider for the patient to document it again or to provide better documentation. The physician or healthcare provider for the patient can add that condition to an existing note or patient report, or create a new note or report, for instance, through their EMR (electronic medical records) within the hospital. As described above, the EMR is entered into the hospital system and, in turn, makes its way into the real-time medical communication system, allowing the real-time medical communication system to recalculate the likelihood of DDO of the clinical documentation for the patient. The real-time medical communication system may, in some embodiments, retain patient data around for a brief period of time. For example, if a patient is discharged in the morning, the patient's data may not be removed from the system until midnight that day. Since record alerts can be timely generated and promptly communicated to users, users can log in to the real-time medical communication system and correct/update the patient's records with additional input or view/lookup update the patient's records until the expiration time.

In this way, the real-time medical communication system can provide plenty of opportunities for CDI and close the loop on the insufficiency of documentation. A technical effect is that DDOs can be detected, reduced, prevented, or even eliminated. A real world benefit can be that, by doing so, the likelihood of payment being made to a claim of a condition for the patient is increased.

Figure 8B:
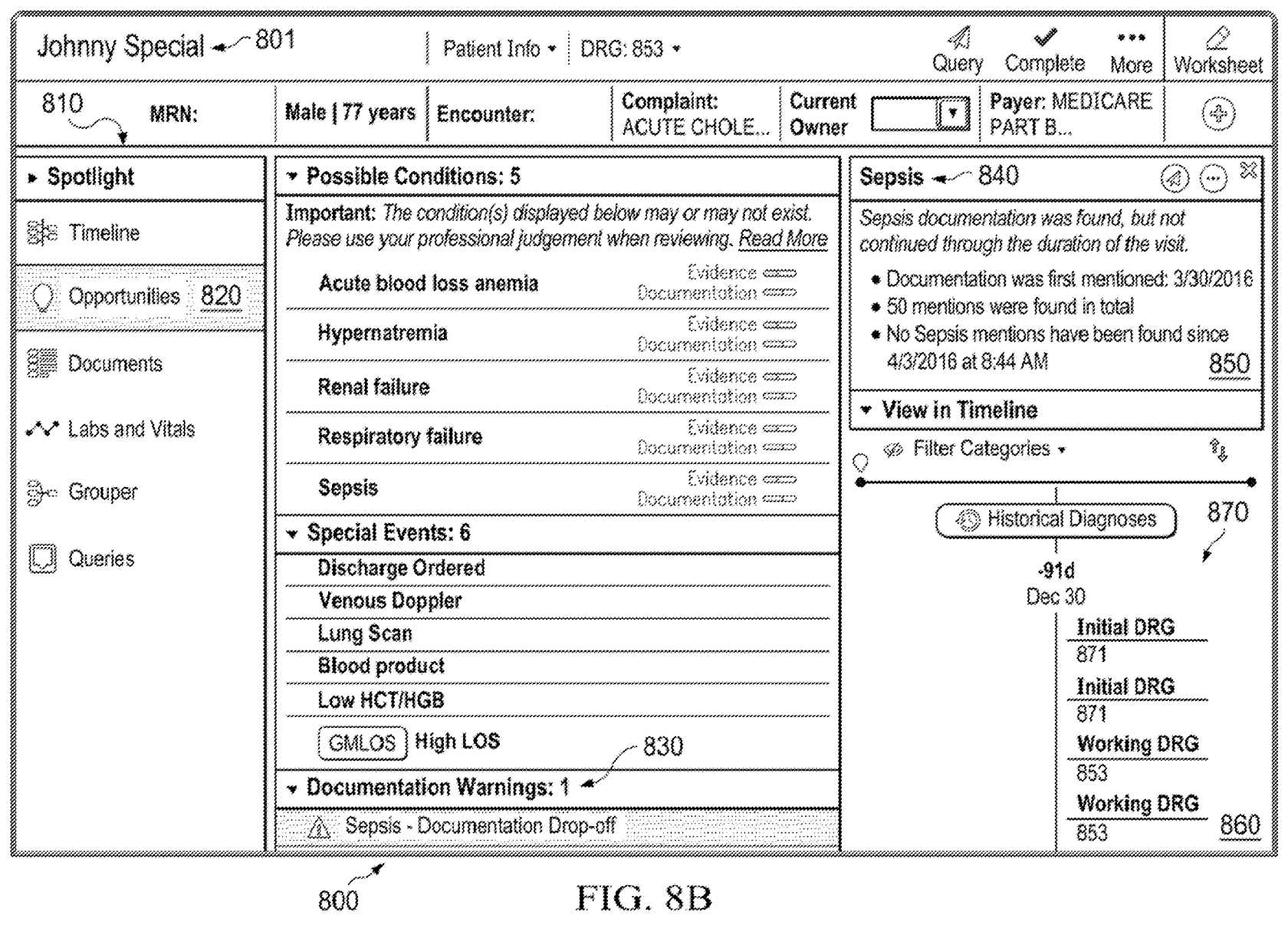

FIGS. 8A-8E are diagrammatic representation of screenshots of user interface 800 for CDI specialist 801. FIG. 8A shows that CDI specialist 801 can navigate, using menu 810 of user interface 800, from a detailed view of a patient data page to "opportunities" page or screen 820. In this example, screen 820 displays a view of "possible conditions" identified by the DDO detection module utilizing static prediction models. Of these possible conditions, the system identifies to CDI specialist 801, through documentation warnings 830 that condition 840 likely has a DDO issue. As described above, this DDO warning can be triggered by an alert generated by alerts engine 290 which, in turn, can be triggered by an output from DDO detector 286.

As illustrated in FIG. 8B, CDI specialist 801 can drill down documentation warnings 830 to review the specifics about the DDO associated with condition 840. In response, user interface 800 displays, in view 850, details about the DDO associated with condition 840. In the example of FIG. 8B, user interface 800 is further configured for displaying timeline 870 in view 860. Timeline 870 can include information received by the real-time medical communication system about the patient's stay (e.g., from admission to current time).

Figure 8C:
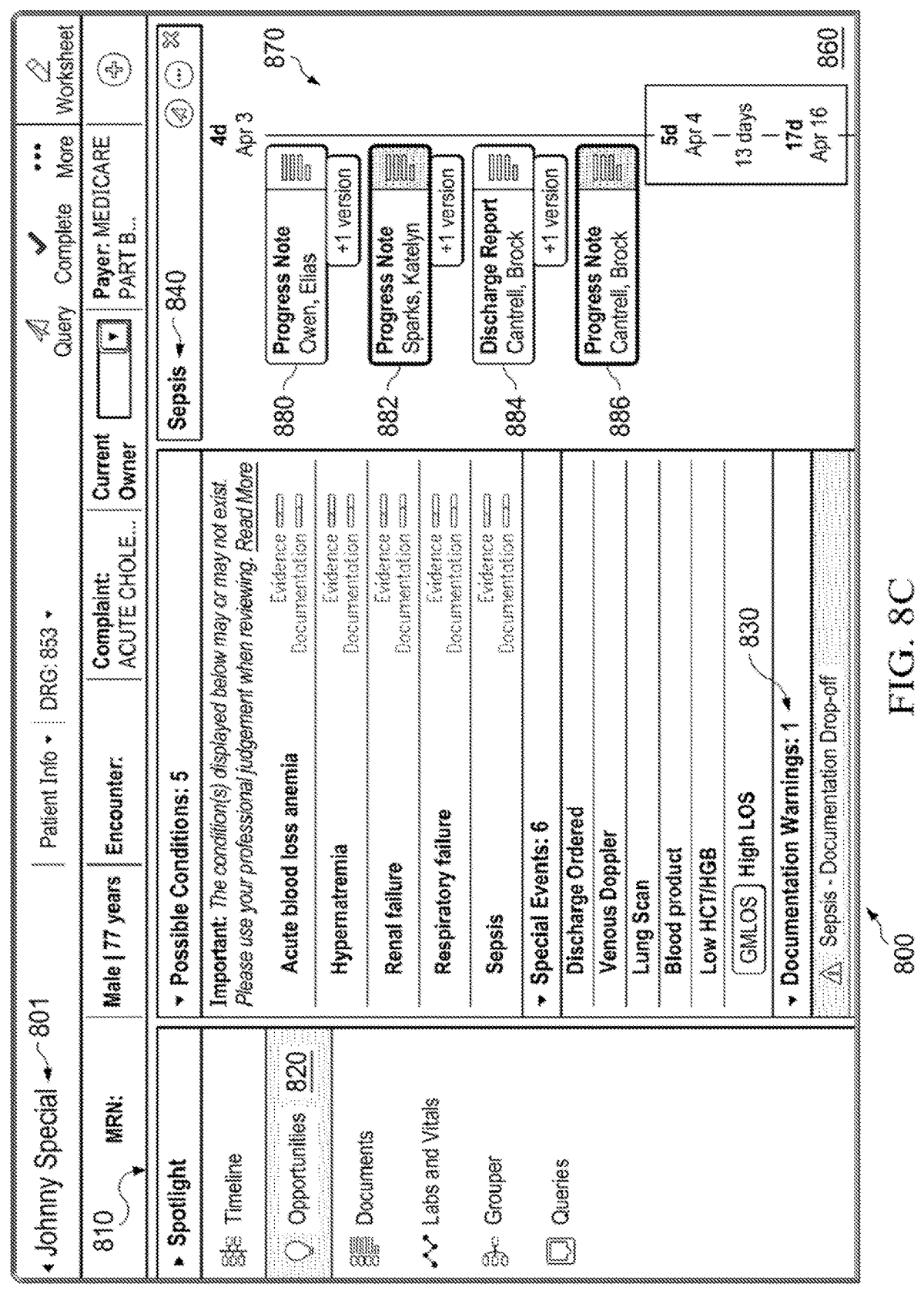

Responsive to documentation warnings 830 warning that DDO likely occurred for condition 840, CDI specialist 801 can scroll down timeline 870 to review how condition 840 is documented during the patient's stay. In the example of FIG. 8C, timeline 870 shows that the patient has four documents 880, 882, 884, and 886 on day 4 of the patient's stay. However, only two of the four documents (882, 886) mention condition 840.

Figure 8D:
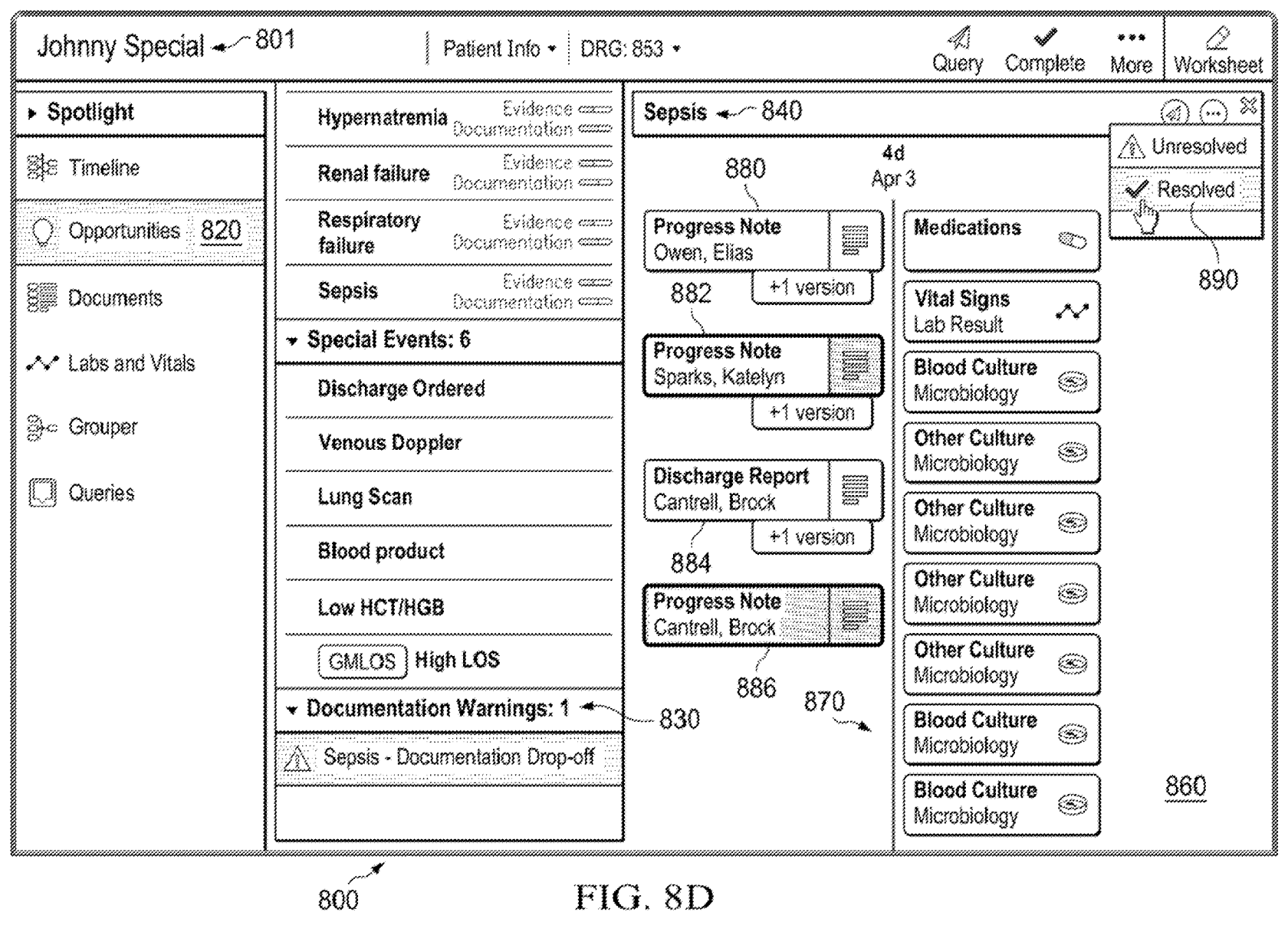
Figure 8E:
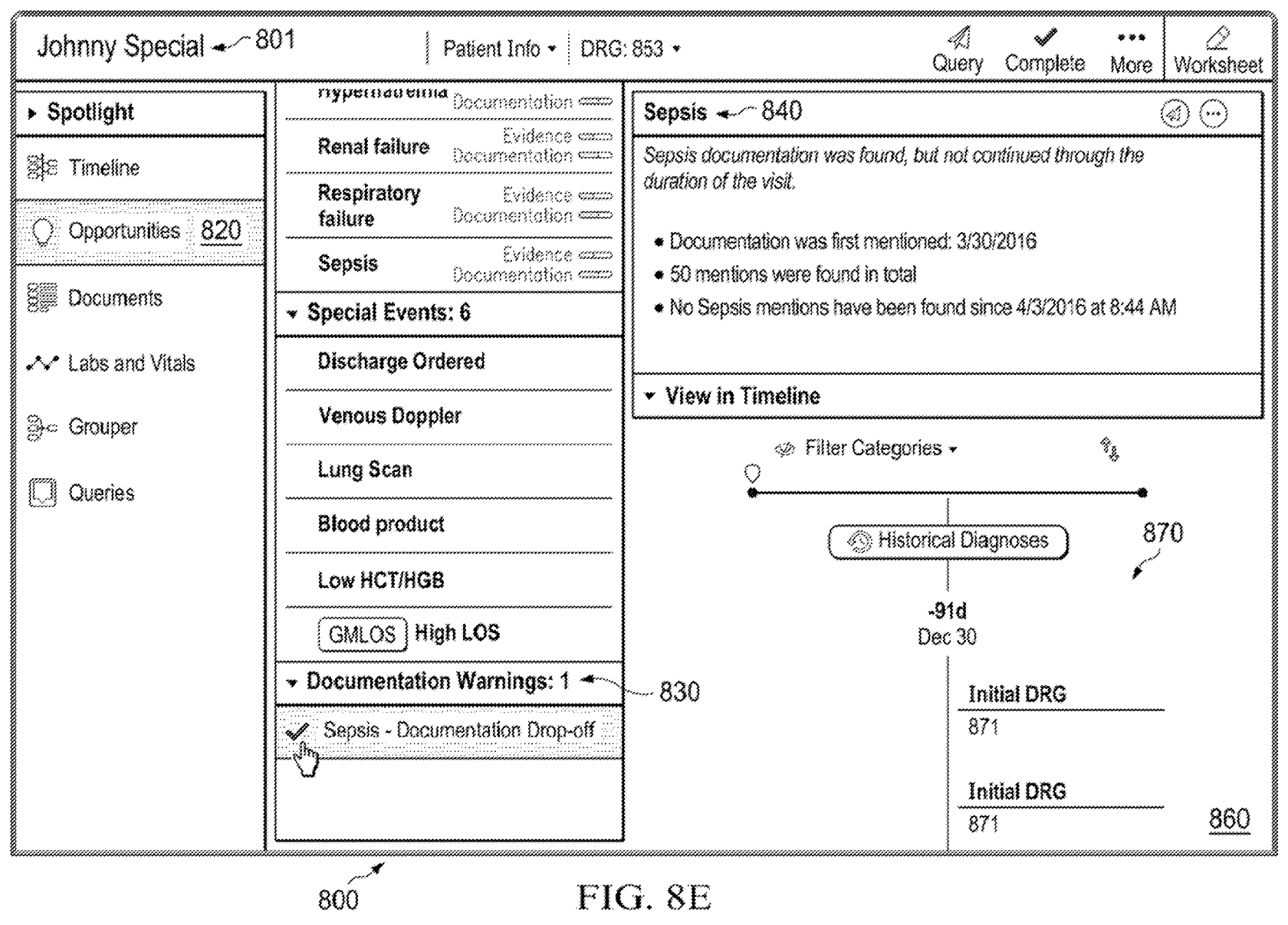

CDI specialist 801 can review timeline 870 and/or documents received during the patient's stay and determine whether to contact the patient's attending physician or healthcare professional to resolve documentation warnings 830. Once CDI specialist 801 determines that the DDO issue for condition 840 identified by the system has been resolved, CDI specialist 801 can navigate to menu 890 and indicate to the system that the DDO issue for condition 840 indicated in documentation warnings 830 has been resolved, as shown in FIG. 8D. In response, the system updates documentation warnings 830 to show that the DDO issue for condition 840 has been resolved, as shown in FIG. 8E. Alternatively, the system may determine, after DDO detection module 280 recalculates DDO potential for the patient based on updated patient data as described above, that the DDO issue for condition 840 has been resolved and automatically update documentation warnings 830 to show that the DDO issue for condition 840 has been resolved, as shown in FIG. 8E.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary.

While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

Embodiments discussed herein can be implemented in a computer communicatively coupled to a network (for example, the Internet), another computer, or in a standalone computer. As is known to those skilled in the art, a suitable computer can include a central processing unit ("CPU"), at least one read-only memory ("ROM"), at least one random access memory ("RAM"), at least one hard drive ("HD"), and one or more input/output ("I/O") device(s). The I/O devices can include a keyboard, monitor, printer, electronic pointing device (for example, mouse, trackball, stylus, touch pad, etc.), or the like.

ROM, RAM, and HD are computer memories for storing computer-executable instructions executable by the CPU or capable of being compiled or interpreted to be executable by the CPU. Suitable computer-executable instructions may reside on a computer-readable medium (e.g., ROM, RAM, and/or HD), hardware circuitry or the like, or any combination thereof. Within this disclosure, the term "computer-readable medium" is not limited to ROM, RAM, and HD and can include any type of data storage medium that can be read by a processor. For example, a computer-readable medium may refer to a data cartridge, a data backup magnetic tape, a floppy diskette, a flash memory drive, an optical data storage drive, a CD-ROM, ROM, RAM, HD, or the like. The processes described herein may be implemented in suitable computer-executable instructions that may reside on a computer-readable medium (for example, a disk, CD-ROM, a memory, etc.). Alternatively, the computer-executable instructions may be stored as software code components on a direct access storage device array, magnetic tape, floppy diskette, optical storage device, or other appropriate computer-readable medium or storage device.

Any suitable programming language can be used to implement the routines, methods or programs of embodiments of the invention described herein, including C, C++, Java, JavaScript, HTML, or any other programming or scripting code, etc. Other software/hardware/network architectures may be used. For example, the functions of the disclosed embodiments may be implemented on one computer or shared/distributed among two or more computers in or across a network. Communications between computers implementing embodiments can be accomplished using any electronic, optical, radio frequency signals, or other suitable methods and tools of communication in compliance with known network protocols.

Different programming techniques can be employed such as procedural or object oriented. Any particular routine can execute on a single computer processing device or multiple computer processing devices, a single computer processor or multiple computer processors. Data may be stored in a single storage medium or distributed through multiple storage mediums, and may reside in a single database or multiple databases (or other data storage techniques). Although the steps, operations, or computations may be presented in a specific order, this order may be changed in different embodiments. In some embodiments, to the extent multiple steps are shown as sequential in this specification, some combination of such steps in alternative embodiments may be performed at the same time. The sequence of operations described herein can be interrupted, suspended, or otherwise controlled by another process, such as an operating system, kernel, etc. The routines can operate in an operating system environment or as stand-alone routines. Functions, routines, methods, steps, and operations described herein can be performed in hardware, software, firmware, or any combination thereof.

Embodiments described herein can be implemented in the form of control logic in software or hardware or a combination of both. The control logic may be stored in an information storage medium, such as a computer-readable medium, as a plurality of instructions adapted to direct an information processing device to perform a set of steps disclosed in the various embodiments. Based on the disclosure and teachings provided herein, a person of ordinary skill in the art will appreciate other ways and/or methods to implement the invention.

It is also within the spirit and scope of the invention to implement in software programming or code an of the steps, operations, methods, routines or portions thereof described herein, where such software programming or code can be stored in a computer-readable medium and can be operated on by a processor to permit a computer to perform any of the steps, operations, methods, routines or portions thereof described herein. The invention may be implemented by using software programming or code in one or more digital computers, by using application specific integrated circuits, programmable logic devices, field programmable gate arrays, optical, chemical, biological, quantum or nanoengineered systems, components and mechanisms may be used. In general, the functions of the invention can be achieved by any means as is known in the art. For example, distributed, or networked systems, components and circuits can be used. In another example, communication or transfer (or otherwise moving from one place to another) of data may be wired, wireless, or by any other means.

A "computer-readable medium" may be any medium that can contain, store, communicate, propagate, or transport the program for use by or in connection with the instruction execution system, apparatus, system or device. The computer-readable medium can be, by way of example only but not by limitation, an electronic, magnetic, optical, electromagnetic, infrared, or semiconductor system, apparatus, system, device, propagation medium, or computer memory. Such computer-readable medium shall be machine readable and include software programming or code that can be human readable (e.g., source code) or machine readable (e.g., object code). Examples of non-transitory computer-readable media can include random access memories, read-only memories, hard drives, data cartridges, magnetic tapes, floppy diskettes, flash memory drives, optical data storage devices, compact-disc read-only memories, and other appropriate computer memories and data storage devices. In an illustrative embodiment, some or all of the software components may reside on a single server computer or on any combination of separate server computers. As one skilled in the art can appreciate, a computer program product implementing an embodiment disclosed herein may comprise one or more non-transitory computer-readable media storing computer instructions translatable by one or more processors in a computing environment.

A "processor" includes any hardware system, mechanism, or component that processes data, signals or other information. A processor can include a system with a central processing unit, multiple processing units, dedicated circuitry for achieving functionality, or other systems. Processing need not be limited to a geographic location, or have temporal limitations. For example, a processor can perform its functions in "real-time," "offline," in a "batch mode," etc.

Portions of processing can be performed at different times and at different locations, by different (or the same) processing systems.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/figures should be considered only as exemplary, and not limiting, unless otherwise specifically noted.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited to only those elements but may include other elements not expressly listed or inherent to such process, product, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein and throughout the claims that follow, the meaning of "in" includes "in" and "on" unless the context clearly dictates otherwise. The scope of the present disclosure should be determined by the following claims and their legal equivalents.

What is claimed is:

1. A method for detecting documentation drop-offs for clinical documentation improvement (CDI), the method comprising:
   receiving, by a CDI processor having a time-sensitive component, a notification that patient data in a data store has been updated, the patient data comprising patient records;
   retrieving, by the CDI processor, the patient records from the data store, the patient records including timestamps and grouped concepts for a patient during a visit;
   for each medical condition of a plurality of medical conditions:
      determining, by the time-sensitive component based on the grouped concepts, whether the each medical condition of the patient was documented at each of the timestamps;
      generating, by the time-sensitive component, a time-series of binary indicators indicating a temporal pattern of documentation of the medical condition during the visit; and
      determining, by the time-sensitive component utilizing a time-sensitive deep learning model specific to the each medical condition, whether the temporal pattern of documentation of the each medical condition during the visit indicates that the each medical condition is sufficiently documented;
   generating, by the time-sensitive component, a running total of medical conditions sufficiently documented during the visit;
   comparing, by the CDI processor, the running total of medical conditions sufficiently documented for the patient during the visit with a list of medical conditions documented for the patient during the visit;
   based on the comparing, determining, by the CDI processor, whether a documentation drop-off for any of the list of medical conditions documented for the patient during the visit has occurred; and
   sending a documentation drop-off notification to a CDI specialist.

2. The method according to claim 1, further comprising:
   validating the each medical condition utilizing a non-time-sensitive prediction model.

3. The method according to claim 1, wherein the CDI processor has a non-time-sensitive component implementing a non-time-sensitive machine learning model trained to determine, on a per condition basis, whether a condition of the patient was documented during the visit.

4. The method according to claim 3, wherein the list of medical conditions documented for the patient during the visit is validated by the non-time-sensitive component.

5. The method according to claim 3, wherein determination of whether the documentation drop-off for any of the list of medical conditions documented for the patient during the visit has occurred comprises processing outcomes from the time-sensitive deep learning model and the non-time-sensitive machine learning model and determining, based on predefined thresholds, whether to trigger a documentation drop-off alert.

6. The method according to claim 1, wherein sending the documentation drop-off notification comprises presenting, through a user interface, a view of the list of medical conditions documented for the patient during the visit and identifying, through a documentation warning, which of the list of medical conditions has a documentation drop-off issue.

7. The method according to claim 1, further comprising:
   presenting, through a user interface, a timeline for the patient during the visit, the timeline showing the list of medical conditions documented for the patient during the visit.

8. A system for detecting documentation drop-offs for clinical documentation improvement (CDI), the system comprising:
   a processor;
   a non-transitory computer-readable medium; and
   stored instructions translatable by the processor to implement a CDI processor having a time-sensitive component, the instructions when translated by the processor perform:
      receiving a notification that patient data in a data store has been updated, the patient data comprising patient records;
      retrieving the patient records from the data store, the patient records including timestamps and grouped concepts for a patient during a visit;
      for each medical condition of a plurality of medical conditions:
         determining, by the time-sensitive component based on the grouped concepts, whether the each medical condition of the patient was documented at each of the timestamps;
         generating, by the time-sensitive component, a time-series of binary indicators indicating a temporal pattern of documentation of the medical condition during the visit; and
         determining, by the time-sensitive component utilizing a time-sensitive deep learning model specific to the each medical condition, whether the temporal pattern of documentation of the each medical condition during the visit indicates that the each medical condition is sufficiently documented;

generating a running total of medical conditions sufficiently documented during the visit;

comparing the running total of medical conditions sufficiently documented for the patient during the visit with a list of medical conditions documented for the patient during the visit;

based on the comparing, determining whether a documentation drop-off for any of the list of medical conditions documented for the patient during the visit has occurred; and sending a documentation drop-off notification to a CDI specialist.

9. The system of claim 8, wherein the instructions when translated by the processor further perform:

validating the each medical condition utilizing a non-time-sensitive prediction model.

10. The system of claim 8, wherein the CDI processor has a non-time-sensitive component implementing a non-time-sensitive machine learning model trained to determine, on a per condition basis, whether a condition of the patient was documented during the visit.

11. The system of claim 10, wherein the list of medical conditions documented for the patient during the visit is validated by the non-time-sensitive component.

12. The system of claim 10, wherein determination of whether the documentation drop-off for any of the list of medical conditions documented for the patient during the visit has occurred comprises processing outcomes from the time-sensitive deep learning model and the non-time-sensitive machine learning model and determining, based on predefined thresholds, whether to trigger a documentation drop-off alert.

13. The system of claim 8, wherein sending the documentation drop-off notification comprises presenting, through a user interface, a view of the list of medical conditions documented for the patient during the visit and identifying, through a documentation warning, which of the list of medical conditions has a documentation drop-off issue.

14. The system of claim 8, wherein the instructions when translated by the processor further perform:

presenting, through a user interface, a timeline for the patient during the visit, the timeline showing the list of medical conditions documented for the patient during the visit.

15. A computer program product for detecting documentation drop-offs for clinical documentation improvement (CDI), the computer program product comprising a non-transitory computer-readable medium storing instructions translatable by a processor to implement a CDI processor having a time-sensitive component, the instructions when translated by the processor perform:

receiving a notification that patient data in a data store has been updated, the patient data comprising patient records;

retrieving the patient records from the data store, the patient records including timestamps and grouped concepts for a patient during a visit;

for each medical condition of a plurality of medical conditions:

determining, by the time-sensitive component based on the grouped concepts, whether the each medical condition of the patient was documented at each of the timestamps;

generating, by the time-sensitive component, a time-series of binary indicators indicating a temporal pattern of documentation of the medical condition during the visit; and determining, by the time-sensitive component utilizing a time-sensitive deep learning model specific to the each medical condition, whether the temporal pattern of documentation of the each medical condition during the visit indicates that the each medical condition is sufficiently documented;

generating a running total of medical conditions sufficiently documented during the visit;

comparing the running total of medical conditions sufficiently documented for the patient during the visit with a list of medical conditions documented for the patient during the visit;

based on the comparing, determining whether a documentation drop-off for any of the list of medical conditions documented for the patient during the visit has occurred; and sending a documentation drop-off notification to a CDI specialist.

16. The computer program product of claim 15, wherein the instructions when translated by the processor further perform:

validating the each medical condition utilizing a non-time-sensitive prediction model.

17. The computer program product of claim 15, wherein the CDI processor has a non-time-sensitive component implementing a non-time-sensitive machine learning model trained to determine, on a per condition basis, whether a condition of the patient was documented during the visit.

18. The computer program product of claim 17, wherein determination of whether the documentation drop-off for any of the list of medical conditions documented for the patient during the visit has occurred comprises processing outcomes from the time-sensitive deep learning model and the non-time-sensitive machine learning model and determining, based on predefined thresholds, whether to trigger a documentation drop-off alert.

19. The computer program product of claim 15, wherein sending the documentation drop-off notification comprises presenting, through a user interface, a view of the list of medical conditions documented for the patient during the visit and identifying, through a documentation warning, which of the list of medical conditions has a documentation drop-off issue.

20. The computer program product of claim 15, wherein the instructions when translated by the processor further perform:

presenting, through a user interface, a timeline for the patient during the visit, the timeline showing the list of medical conditions documented for the patient during the visit.

* * * * *